(12) United States Patent
Niu et al.

(10) Patent No.: US 7,031,894 B2
(45) Date of Patent: Apr. 18, 2006

(54) GENERATING A LIBRARY OF SIMULATED-DIFFRACTION SIGNALS AND HYPOTHETICAL PROFILES OF PERIODIC GRATINGS

(75) Inventors: Xinhui Niu, Los Altos, CA (US); Nickhil Jakatdar, Los Altos, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 924 days.

(21) Appl. No.: 10/051,830

(22) Filed: Jan. 16, 2002

(65) Prior Publication Data
US 2003/0200063 A1    Oct. 23, 2003

(51) Int. Cl.
G06G 7/48    (2006.01)
(52) U.S. Cl. ........................................... 703/6
(58) Field of Classification Search .................... 703/6, 703/2; 356/305, 328, 902
See application file for complete search history.

(56) References Cited

U.S. PATENT DOCUMENTS

| | | | |
|---|---|---|---|
| 4,513,384 A | 4/1985 | Rozencwaig | |
| 5,477,363 A | 12/1995 | Matsuda | |
| 5,701,013 A | 12/1997 | Hsia et al. | |
| 6,146,032 A * | 11/2000 | Dunham | 400/120.18 |
| 6,177,680 B1 | 1/2001 | Dick et al. | |
| 6,407,396 B1 | 6/2002 | Mih et al. | |
| 6,479,166 B1 | 11/2002 | Heuer et al. | |
| 6,713,753 B1 * | 3/2004 | Rovira et al. | 250/225 |
| 6,891,626 B1 * | 5/2005 | Niu et al. | 356/625 |
| 6,898,537 B1 * | 5/2005 | McGahan | 702/76 |

OTHER PUBLICATIONS

N. W. Ashcroft et al., "Solid State Physics", Saunders College, Philadelphia, 1976, pp. 133-134.
Ch. M. Bishop, "Neural Networks for Pattern Recognition", Clarendon Press-Oxford, 1995, Ch. 4,, pp. 116-163.
O. S. Heavens, "Optical Properties of Thin Solid Films", Dover Publications Inc. N. Y. 1991 (book).
M. G. Moharam et al., "Rigorous coupled-wave analysis of planar-grating diffraction", J. Opt. Soc. Am. vol. 71, No. 7/Jul. 1981, pp. 811-818.
W. H. Press et al., "Numerical Recipes", Cambridge University Press, 1986 (book).

(Continued)

*Primary Examiner*—Albert W. Paladini
(74) *Attorney, Agent, or Firm*—Morrison & Foerster LLP

(57) ABSTRACT

A library of simulated-diffraction signals and hypothetical profiles of a periodic grating can be generated by generating diffraction calculations for a plurality of blocks of hypothetical layers. A diffraction calculation for a block of hypothetical layers characterizes, in part, the behavior of a diffraction beam in the block of hypothetical layers. Each block of hypothetical layers includes two or more hypothetical layers, and each hypothetical layer characterizes a layer within a hypothetical profile. The diffraction calculations for the blocks of hypothetical layers are stored prior to generating the library. The simulated-diffraction signals to be stored in the library are then generated based on the stored diffraction calculations for the blocks of hypothetical layers.

42 Claims, 27 Drawing Sheets

OTHER PUBLICATIONS

J. A. Rice, "Mathematical Statistics and Data Analysis" sec. ed., ch. 14, Duxbury Press, 1995, pp. 507-570.

Azzam et al., "Ellipsometry and Polarized Light", North Holland library, Amsterdam, 1987, book.

Moharam et al., "Stable implementation of the rigorous coupled-wave analysis for surface—relief gratings: enhanced transmittance matrix approach", J. Opt. Soc. Am. vol. 12, No. 5, May 1995, pp. 1077-1086.

R. T. Chen et al., "Si-Based Surface-Relief Polygonal Gratings for 1-to-Many Wafer Scale Optical Clock Signal Distribution", IEEE Photonics Technology Letters, vol. 8, No. 8, Aug. 1996, pp. 1038-1040.

T. Khayim et al., "Ultrafast Unidirectional Deflection by Electrooptic Traveling Phase Grating Using Periodic Domain Inversion", IEEE, CLEO/Pacific Rim '99/Th03, 1999, pp. 726-727.

S. Pelissier et al., "Fabrication of Buried Corrugated Waveguides by Wafer Direct Bonding", IEEE J. of Lightwave Tech. vol. 18, No. 4, Apr. 2000.

B. Pezeshki et al., "400-mW Single-Frequency 660-nm Semiconductor Laser", IEEE Photonics Tech. Letters, vol. 11, No. 7, Jul. 1999, pp. 791-793.

* cited by examiner

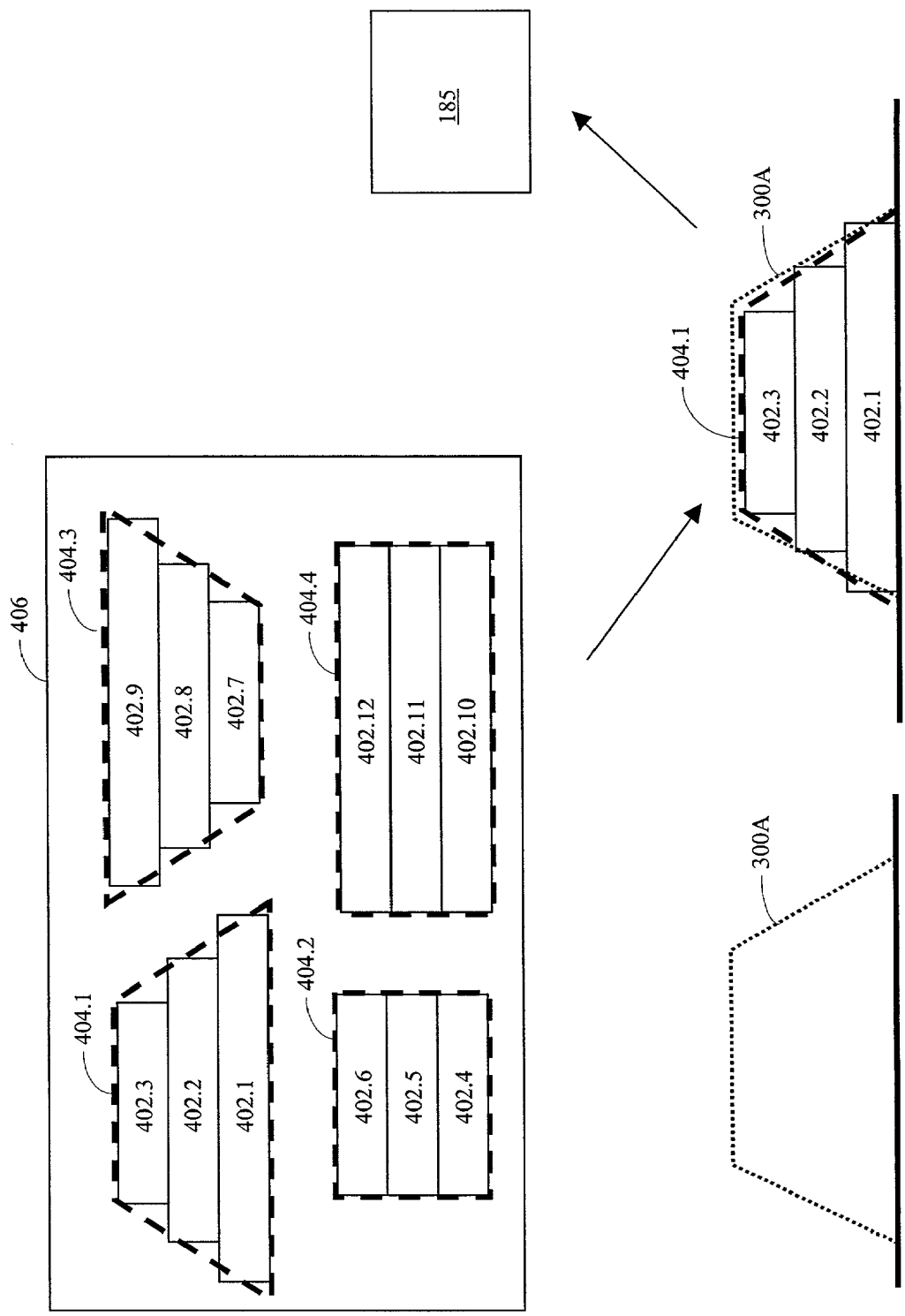

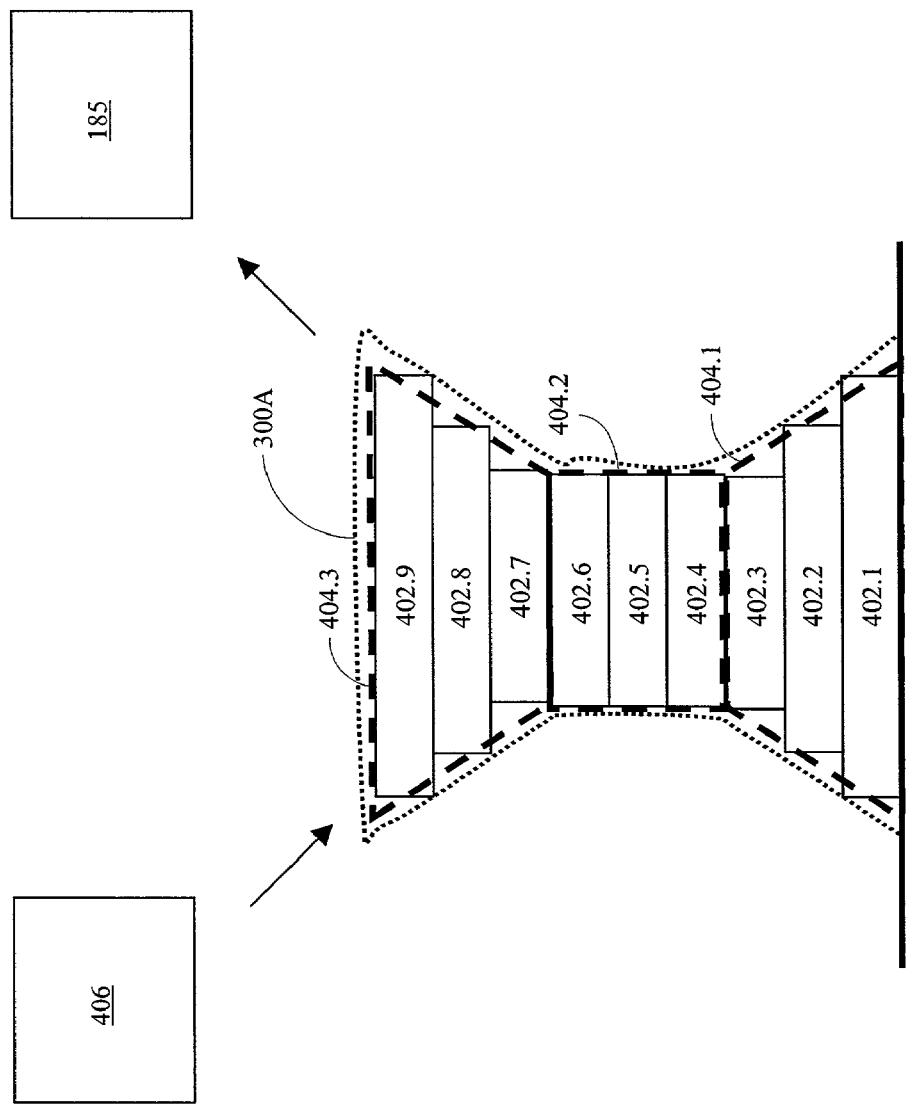

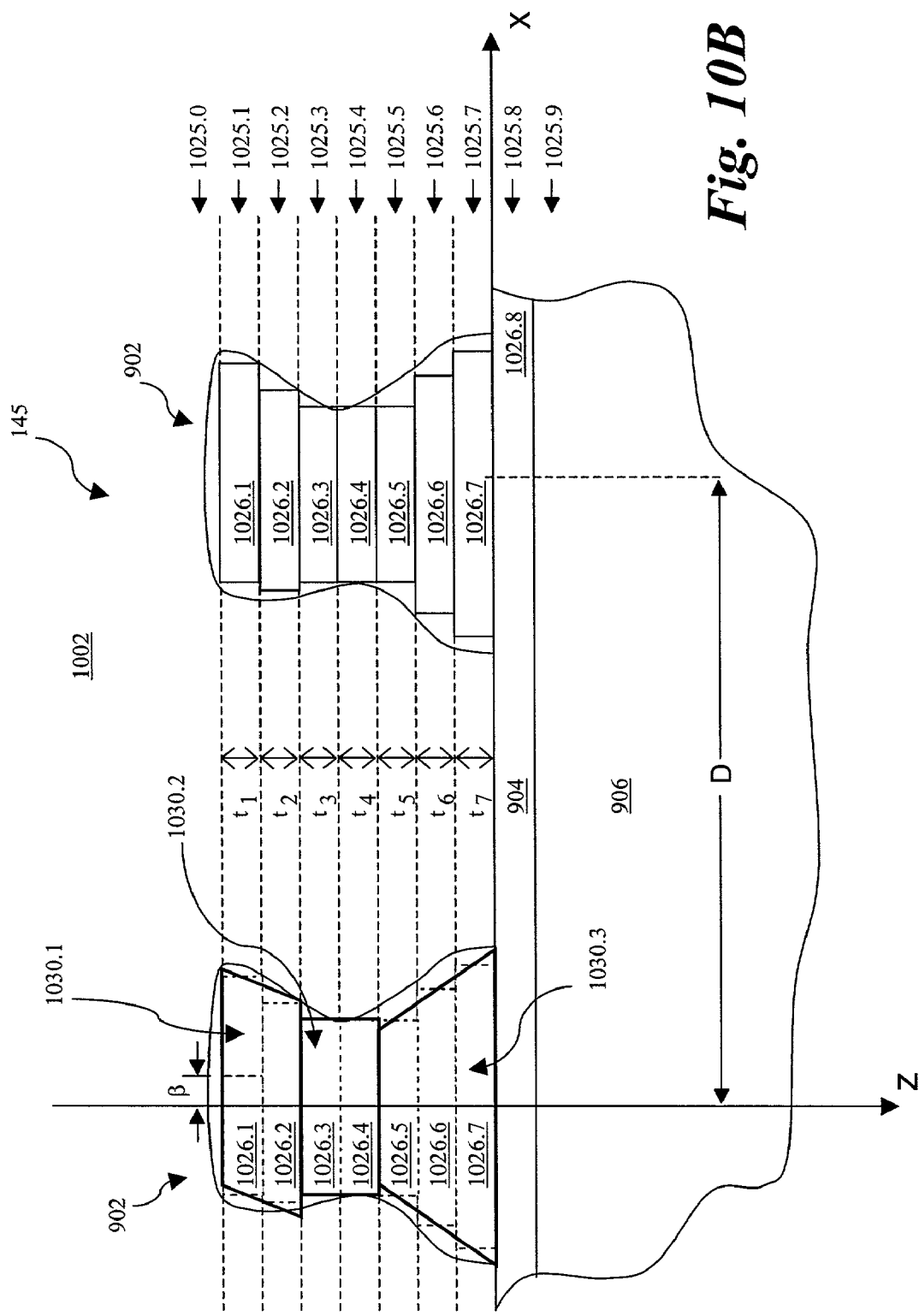

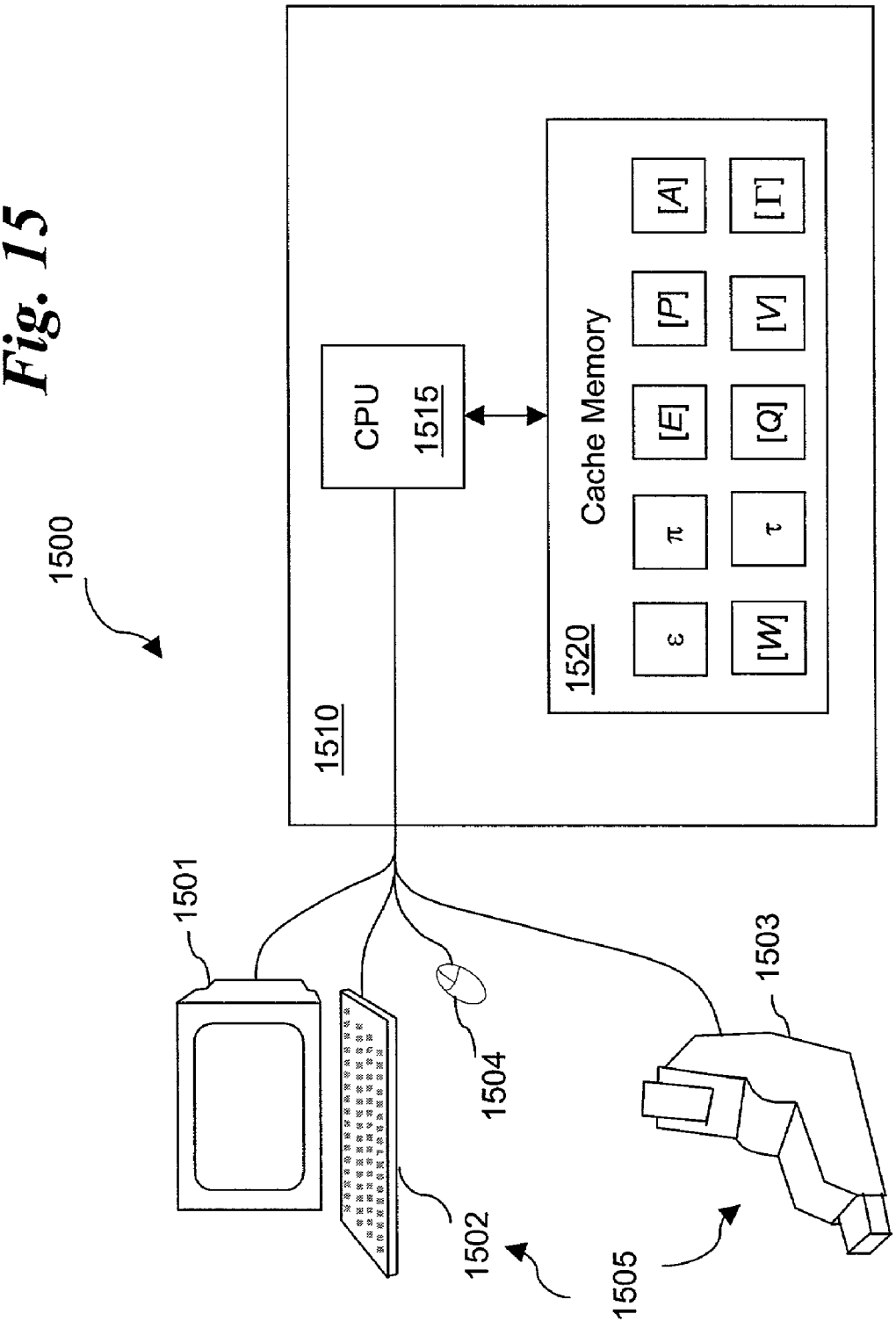

Continuation

GENERATING A LIBRARY OF SIMULATED-DIFFRACTION SIGNALS AND HYPOTHETICAL PROFILES OF PERIODIC GRATINGS

BACKGROUND

1. Field of the Invention

The present invention relates to wafer metrology, and more particularly to generating a library of simulated-diffraction signals for use in optical metrology to determine the profile of periodic gratings.

2. Related Art

In semiconductor manufacturing, periodic gratings are typically utilized for quality assurance. For example, one typical use of such periodic gratings includes fabricating a periodic grating in proximity to the operating structure of a semiconductor chip. By determining the profile of the periodic grating, the quality of the fabrication process utilized to form the periodic grating, and by extension the semiconductor chip proximate the periodic grating, can be evaluated.

Optical metrology can be utilized to determine the profile of a periodic grating. In general optical metrology involves directing an incident beam at the periodic grating, and measuring the resulting diffraction beam. The characteristics of the measured-diffraction beam (i.e., a measured-diffraction signal) is typically compared to a library of pre-determined diffraction signals (i.e., hypothetical-diffraction signals) that are associated with known profiles. When a match is made between the measured-diffraction signal and one of the hypothetical-diffraction signals, then the profile associated with the matching hypothetical-diffraction signal is presumed to represent the profile of the periodic grating.

In general, the process of generating a hypothetical-diffraction signal involves performing a large number of complex calculations, which can be time and computationally intensive. The amount of time and computational capability and capacity needed to generate hypothetical-diffraction signals can limit the size and resolution (i.e., the number of entries and the increment between entries) of the library of hypothetical-diffraction signals that can be generated.

SUMMARY

In one exemplary embodiment, a library of simulated-diffraction signals and hypothetical profiles of a periodic grating is generated by generating diffraction calculations for a plurality of blocks of hypothetical layers. A diffraction calculation for a block of hypothetical layers characterizes, in part, the behavior of a diffraction beam in the block of hypothetical layers. Each block of hypothetical layers includes two or more hypothetical layers, and each hypothetical layer characterizes a layer within a hypothetical profile. The diffraction calculations for the blocks of hypothetical layers are stored prior to generating the library. The simulated-diffraction signals to be stored in the library are then generated based on the stored diffraction calculations for the blocks of hypothetical layers.

DESCRIPTION OF DRAWING FIGURES

The present invention can be best understood by reference to the following description taken in conjunction with the accompanying drawing figures, in which like parts may be referred to by like numerals:

FIGS. 5A and 5B depict an exemplary process of generating simulated-diffraction signals.

FIGS. 6A and 6B depict another exemplary process of generating simulated-diffraction signals.

FIGS. 10A–10C depict cross sectional views of a portion of a periodic grating.

FIG. 15 is another exemplary computer system.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

Figure 1:
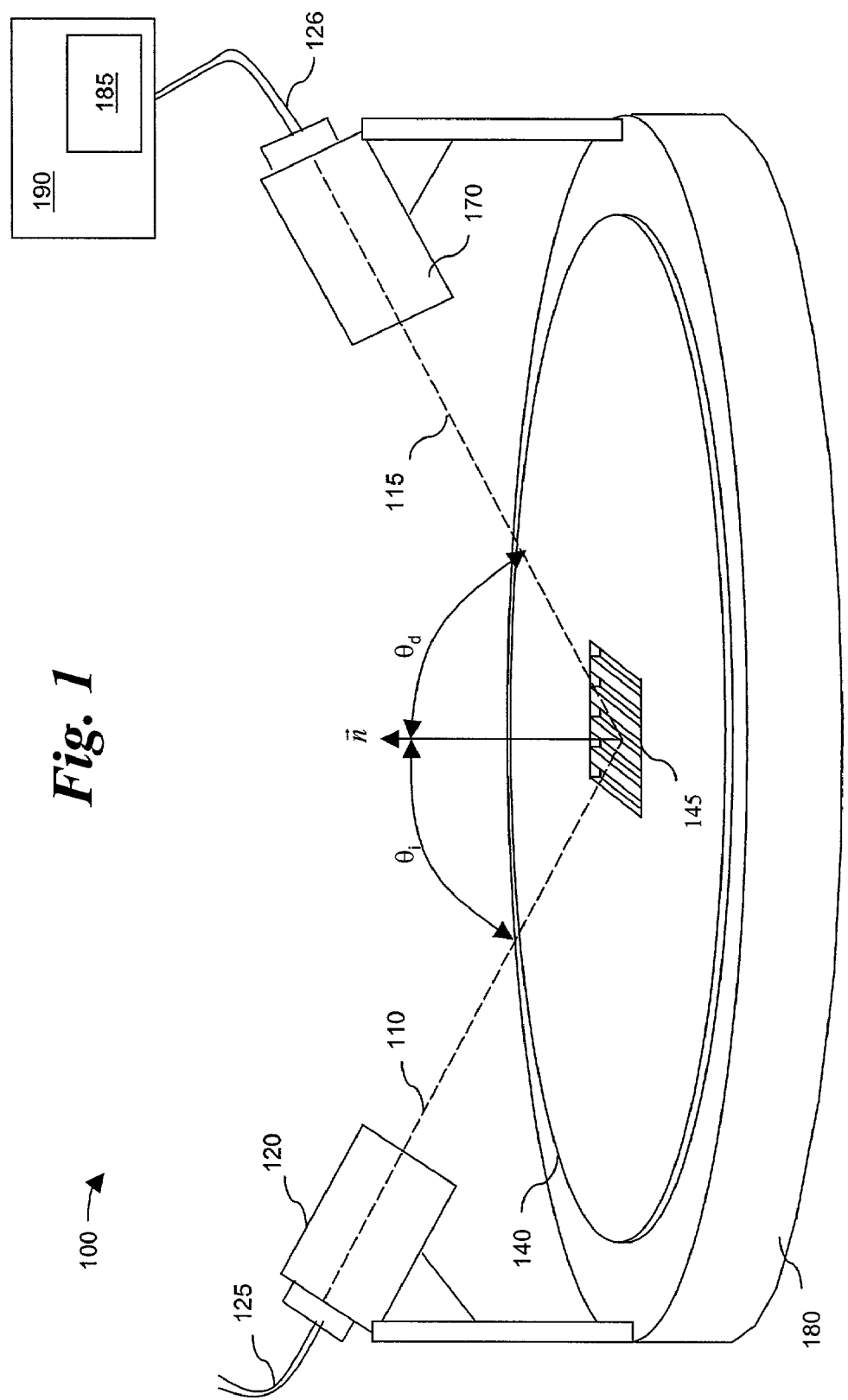
FIG. 1 depicts an exemplary optical-metrology system.

With reference to FIG. 1, a periodic grating 145 is depicted on a semiconductor wafer 140. As depicted in FIG. 1, wafer 140 is disposed on a process plate 180, which can include a chill plate, a hot plate, a developer module, and the like. Alternatively, wafer 140 can also be disposed on a wafer track, in the end chamber of an etcher, in an end-station or metrology station, in a chemical mechanical polishing tool, and the like.

As described earlier, periodic grating 145 can be formed in test areas on wafer 140 that are proximate to or within an operating structure formed on wafer 140. For example, periodic grating 145 can be formed adjacent to a device formed on wafer 140. Alternatively, periodic grating 145 can be formed in an area of the device that does not interfere with the operation of the device. As will be described in greater detail below, the profile of periodic grating 145 is obtained to determine whether periodic grating 145, and by extension the operating structure adjacent periodic grating 145, has been fabricated according to specifications.

1. Optical Metrology

In one exemplary embodiment, optical-metrology can be utilized to obtain the profile of periodic grating 145. As depicted in FIG. 1, an optical-metrology system 100 can include an electromagnetic source 120, such as an ellipsometer, reflectometer, and the like. Periodic grating 145 is illuminated by an incident beam 110 from electromagnetic source 120. Incident beam 110 is directed onto periodic grating 145 at an angle of incidence $\theta_i$ with respect to normal $\vec{n}$ of periodic grating 145. Diffraction beam 115 leaves at an angle of $\theta_d$ with respect to normal $\vec{n}$. In one exemplary embodiment, the angle of incidence $\theta_i$ is near the Brewster's angle. However, the angle of incidence $\theta_i$ can vary depending on the application. For example, in an alternative embodiment, the angle of incidence $\theta_i$ is between about 0 and about 40 degrees. In another embodiment, the angle of incidence $\theta_i$ is between about 30 and about 90 degrees. In still another embodiment, the angle of incidence $\theta_i$ is between about 40 and about 75 degrees. In yet another embodiment, the angle of incidence $\theta_i$ is between about 50 and about 70 degrees.

Electromagnetic source 120 can include focusing optics to control the spot size of incident beam 110. In one embodiment, spot size of incident beam 110 can be reduced to less than the size of the test area on wafer 140 that contains periodic grating 145. For example, a spot size of about 50 μm by 50 μm, or smaller, can be used. Additionally, electromagnetic source 120 can include a pattern recognition module to center the spot in the test area on wafer 140.

As depicted in FIG. 1, diffraction beam 115 is received by detector 170. When electromagnetic source 120 is an ellipsometer, the magnitude ($\Psi$) and the phase ($\Delta$) of diffraction beam 115 are received and detected. When electromagnetic source 120 is a reflectometer, the relative intensity of diffraction beam 115 is received and detected.

To determine the profile of periodic grating 145, optical-metrology system 100 includes a processing module 190, which converts diffraction beam 115 received by detector 170 into a diffraction signal (i.e., a measured-diffraction signal). Processing module 190 then compares the measured-diffraction signal to the simulated-diffraction signals stored in a library 185. As will be described in greater detail below, each simulated-diffraction signal in library 185 is associated with a theoretical profile. When a match is made between the measured-diffraction signal and one of the simulated-diffraction signals in library 185, the theoretical profile associated with the matching simulated-diffraction signal is presumed to represent the actual profile of periodic grating 145. The matching simulated-diffraction signal and/or theoretical profile can then be utilized to determine whether the periodic grating has been fabricated according to specifications.

Although optical-metrology system 100 has been described and depicted thus far as having a single electromagnetic source 120 and a single detector 170, it should be recognized that optical-metrology system 100 can include any number of electromagnetic sources 120 and detectors 170. For example, with reference to FIG. 2, optical-metrology system 100 is depicted with two electromagnetic sources 120A and 120B, and two detectors 170A and 170B. Two incident beams 110A and 110B are generated by electromagnetic sources 120A and 120B, with each incident beam 110A and 110B including two polarizations of the electromagnetic wave to allow for both intensity and phase measurements.

Figure 2:
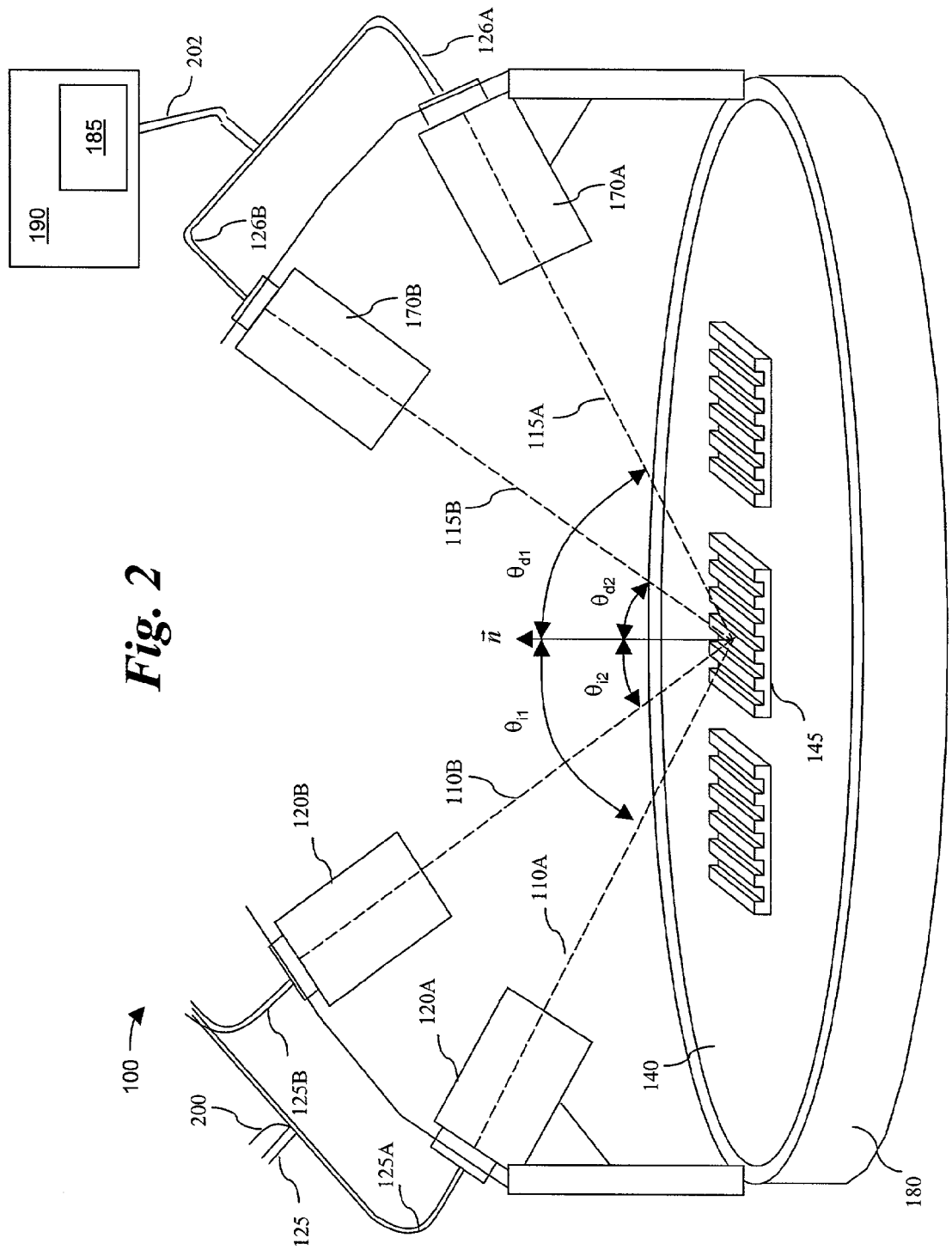
FIG. 2 depicts another exemplary optical-metrology system.

As depicted in FIG. 2, an optical fiber 125 can transport broadband radiation from a source (not shown) to the electromagnetic sources 120A and 120B. A switching mechanism 200 can direct the broadband radiation alternately to the two optic fiber branches 125A and 125B, which lead to the electromagnetic sources 120A and 120B, respectively. In a preferred embodiment, the switching mechanism 200 is a wheel with an opening in one semicircle, so that rotation of the switching wheel 200 by 180 degrees produces a switching of the optic fiber branch 125A or 125B to which the radiation is directed. In this preferred embodiment, the incident beams are directed to wafer 140 so that the angles of incidence $\theta_{i1}$ and $\theta_{i2}$ are approximately 50 and 70 degrees. Other angles of incidence are also contemplated as useful, and angles between zero and 90 degrees are possible. In the present embodiment, incidence $\theta_{i1}$ and $\theta_{i2}$ are chosen to be disparate enough that redundancy of information is not an issue, while both $\theta_{i1}$ and $\theta_{i2}$ are chosen to be close enough to Brewster's angle that the incident beam is sensitive to the grating features.

As depicted in FIG. 2, diffraction beams 115A and 115B leave the wafer at angles $\theta_{d1}$ and $\theta_{d2}$. Diffraction beams 115A and 115B are then received by detectors 170A and 170B. When electromagnetic sources 120A and 120B are ellipsometers, the magnitude ($\Psi$) and the phase ($\Delta$) of diffraction beams 115A and 115B are received and detected. When electromagnetic source 120 is a reflectometer, the relative intensity of diffraction beams 115A and 115B is received and detected.

It should be understood that multiple detectors 170A and 170B are not necessary to perform multiple-angle reflectometry or ellipsometry measurements. Instead, a single electromagnetic source 120 and detector 170 can perform a first measurement for an angle of incidence of $\theta_{i1}$, and then be moved to perform a second measurement for an angle of incidence of $\theta_{i2}$.

2. Library of Simulated-Diffraction Signals and Theoretical Profiles

As described above, with reference again to FIG. 1, library 185 includes simulated-diffraction signals that are associated with theoretical profiles of periodic grating 145. More particularly, in one exemplary embodiment, library 185 includes pairings of simulated-diffraction signals and theoretical profiles of periodic grating 145. The simulated-diffraction signal in each pairing includes theoretically generated reflectances that characterize the predicted behavior of diffraction beam 115 assuming that the profile of the periodic grating 145 is that of the theoretical profile in the simulated-diffraction signal and theoretical profile pairing.

The set of hypothetical profiles stored in library 185 can be generated by characterizing a hypothetical profile using a set of parameters, then varying the set of parameters to generate hypothetical profiles of varying shapes and dimensions. The process of characterizing a profile using a set of parameters can also be referred to as parameterizing.

Figure 3E:
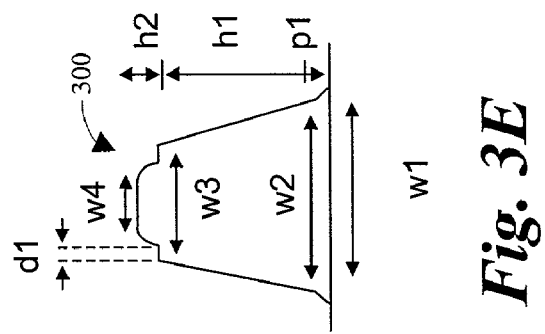
FIGS. 3A–3E depict various hypothetical profiles of periodic gratings.
Figure 3C:
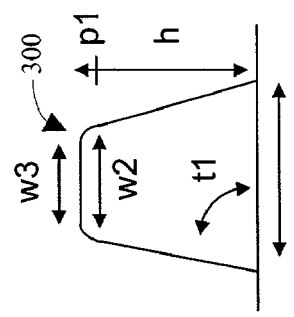
Figure 3D:
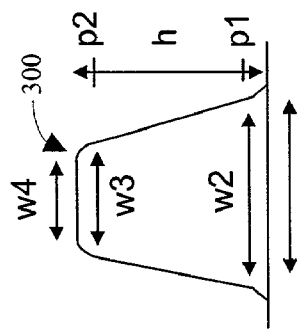
Figure 3A:
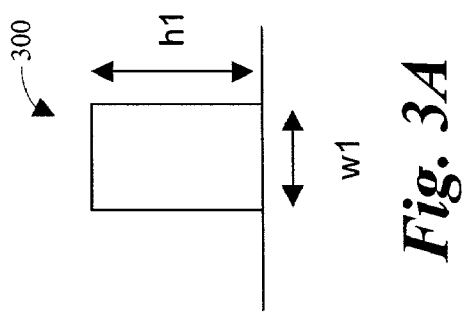
Figure 3B:
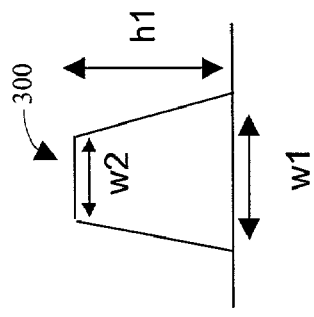

For example, as depicted in FIG. 3A, assume that hypothetical profile 300 can be characterized by parameters h1 and w1 that define its height and width, respectively. As depicted in FIGS. 3B to 3E, additional shapes and features of hypothetical profile 300 can be characterized by increasing the number of parameters. For example, as depicted in FIG. 3B, hypothetical profile 300 can be characterized by parameters h1, w1, and w2 that define its height, bottom width, and top width, respectively. Note that the width of hypothetical profile 300 can be referred to as the critical dimension (CD). For example, in FIG. 3B, parameter w1 and w2 can be described as defining the bottom CD and top CD, respectively, of hypothetical profile 300.

As described above, the set of hypothetical profiles stored in library 185 (FIG. 1) can be generated by varying the parameters that characterize the hypothetical profile. For example, with reference to FIG. 3B, by varying parameters h1, w1, and w2, hypothetical profiles of varying shapes and dimensions can be generated. Note that one, two, or all three parameters can be varied relative to one another.

With reference again to FIG. 1, the number of hypothetical profiles in the set of hypothetical profiles stored in library 185 depends, in part, on the range over which the set of parameters and the increment at which the set of parameters are varied. The range and increment can be selected based on familiarity with the fabrication process for periodic grating 145 and what the range of variance is likely to be. The range and increment can also be selected based on empirical measures, such as measurements using AFM, X-SEM, and the like. For a more detailed description of determining the number of parameters to use in characterizing a hypothetical profile and the range over which to vary the parameters, see U.S. patent application Ser. No. 09/907,488 titled GENERATION OF A LIBRARY OF PERIODIC GRATING DIFFRACTION SIGNALS, filed on Jul. 16, 2001, the entire content of which is incorporated herein by reference.

As described above, the simulated-diffraction signals stored in library 185 can be generated by generating a simulated-diffraction signal for each hypothetical profile in the set of hypothetical profiles stored in library 185. As will be illustrated in more detail below, the process of generating a simulated-diffraction signal can involve performing a large number of complex calculations. Additionally, as the complexity of the theoretical profile increases, so does the number and complexity of the calculations needed to generate the simulated-diffraction signal for the theoretical profile. Furthermore, as the number of theoretical profiles increases, so does the amount of time and processing capacity and capability needed to generate library 185.

As such, in one exemplary embodiment, a portion of the calculations performed in generating simulated-diffraction signals can be stored as intermediate calculations prior to generating library 185. The simulated-diffraction signals for each hypothetical profile in library 185 can then be generated using these intermediate calculations rather than performing all of the calculations needed to generate a simulated-diffraction signal for each theoretical profile in library 185.

More particularly, in one exemplary embodiment, diffraction calculations are generated for a plurality of blocks of hypothetical layers. A diffraction calculation for a block of hypothetical layers characterizes, in part, the behavior of diffraction beam 115 in the block of hypothetical layers. Each block of hypothetical layers includes two or more hypothetical layers, and each hypothetical layer characterizes a layer within a hypothetical profile. The diffraction calculations for the blocks of hypothetical layers are stored prior to generating library 185. The simulated-diffraction signals to be stored in library 185 are generated based on the stored diffraction calculations for the blocks of hypothetical layers.

Figure 4:
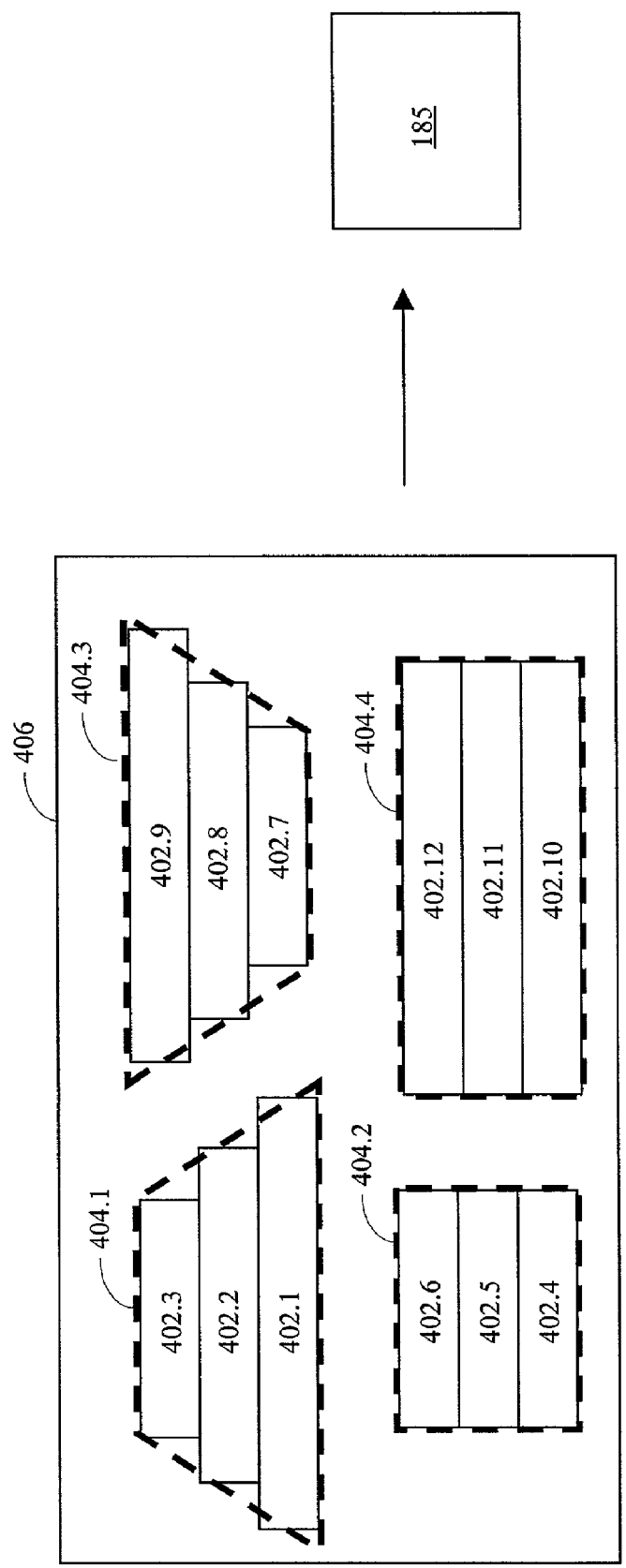
FIG. 4 depicts an exemplary cache and library.

For example, with reference to FIG. 4, a plurality of hypothetical layers 402 (e.g., hypothetical layer 402.1–402.12) can be grouped together as a block of hypothetical layers 404 (e.g., block of hypothetical layers 404.1–404.4). Each hypothetical layer 402 characterizes a layer of a hypothetical profile.

In the present example, hypothetical layers 402.1, 402.2, and 402.3 are depicted as being grouped together to form block of hypothetical layers 404.1. Hypothetical layers 402.4, 402.5, and 402.6 are depicted as being grouped together to form block of hypothetical layers 404.2. Hypothetical layers 402.7, 402.8, and 402.9 are depicted as being grouped together to form block of hypothetical layers 404.3. Hypothetical layers 402.10, 402.11, and 402.12 are depicted as being grouped together to form block of hypothetical layers 404.4. In this manner, a number of blocks of hypothetical layers 404 of various sizes and shapes can be generated. Although blocks of hypothetical layers 404 are depicted in FIG. 4 as including three hypothetical layers 402, it should be recognized that they can include any number of hypothetical layers 402.

Diffraction calculations, which characterize the behavior of diffraction signals, are generated for each hypothetical layer 402 within a block of hypothetical layers 404. Diffraction calculations for each block of hypothetical layers 404 are then generated by aggregating the diffraction calculations for each hypothetical layer 402 within each block of hypothetical layers 404. The diffraction calculations and the blocks of hypothetical layers 404 are then stored. More particularly, in one exemplary embodiment, pairs of diffraction calculations and blocks of hypothetical layers 404 are stored in a cache 406.

For example, for block of hypothetical layers 404.1, diffraction calculations are generated for hypothetical layers 402.1, 402.2, and 402.3. A diffraction calculation for block of hypothetical layers 404.1 is then generated by aggregating diffraction calculations for hypothetical layers 402.1, 402.2, and 402.3. Block of hypothetical layers 404.1 and the diffraction calculations associated with block of hypothetical layers 404.1 are then stored in cache 406. In a similar manner, diffraction calculations for blocks of hypothetical layers 404.2, 404.3, and 404.4 are generated and stored in cache 406.

Although four blocks of hypothetical layers 404 are depicted and described as being generated and stored in cache 406, it should be recognized that any number of blocks of hypothetical layers 404 of various shapes and configurations can be generated and stored in cache 406. Indeed, in use, cache 406 may contain tens and hundreds of thousands of blocks of hypothetical layers 404 and diffraction calculations.

Additionally, although FIG. 4 depicts blocks of hypothetical layers 404 being stored in cache 406 in a graphical format, blocks of hypothetical layers 404 can be stored in various formats. For example, blocks of hypothetical layers 404 can be stored using parameters that define their shapes.

In one exemplary embodiment, simulated-diffraction signals for a set of hypothetical profiles to be stored in library 185 can be generated based on the diffraction calculations for blocks of hypothetical layers 404 stored in cache 406. More particularly, for each hypothetical profile to be stored in library 185, one or more blocks of hypothetical layers 404 that characterize the hypothetical profile are selected from those stored in cache 406. Boundary conditions are then applied to generate the simulated-diffraction signal for the hypothetical profile. The simulated-diffraction signal and the hypothetical profile are then stored in library 185. The hypothetical profile can be stored in various formats, such as graphically, using the parameters that define the hypothetical profile, or both.

In some applications, one block of hypothetical layers 404 can be used to characterize a hypothetical profile. For example, with reference to FIG. 5A, assume for the sake of this example that a simulated-diffraction signal is to be generated for hypothetical profile 300A. As described above, a block of hypothetical layers 404 from cache 406 is selected that characterizes hypothetical profile 300A. The appropriate block of hypothetical layers 404 can be selected using an error minimization algorithm, such as a sum-of-squares algorithm.

As depicted in FIG. 5A, in this example, block of hypothetical layers 404.1 is selected from cache 406. The diffraction calculation associated with block of hypothetical layers 404.1 is then retrieved from cache 406. Boundary conditions are then applied to generate the simulated-diffraction signal for hypothetical profile 300A. The simulated-diffraction signal and hypothetical profile 300A are then stored in library 185.

As described above, the parameters that define hypothetical profile 300A can be varied to define another hypothetical profile. In this example, with reference to FIG. 5B, assume that the parameters are varied to define hypothetical profile 300B.

Figure 5B:
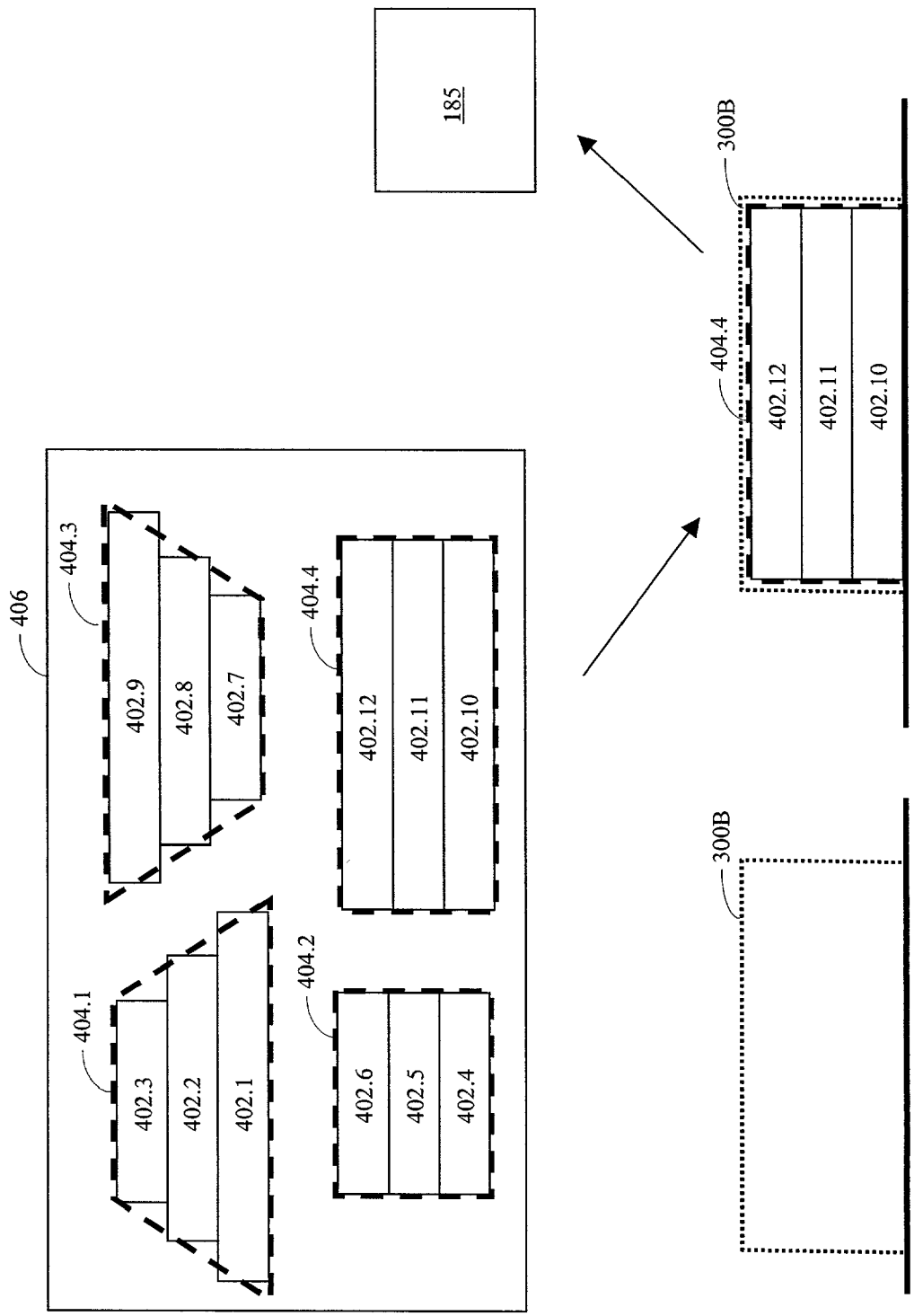

As depicted in FIG. 5B, block of hypothetical layers 404.4 is selected from cache 406. The diffraction calculation associated with block of hypothetical layers 404.4 is then retrieved from cache 406. Boundary conditions are then applied to generate the simulated-diffraction signal for hypothetical profile 300B. The simulated-diffraction signal and hypothetical profile 300B are then stored in library 185.

In this manner, any number of hypothetical profiles and simulated-diffraction signals can be generated and stored in library 185 using blocks of hypothetical layers 404 and the diffraction calculations in cache 406. As described above, in the present exemplary embodiment, blocks of hypothetical layers 404 and the diffraction calculations in cache 406 are generated before generating library 185. As such, the calculations needed to generate the diffraction calculations associated with blocks of hypothetical layers 404 do not need to be performed at the time that library 185 is generated. This can have the advantage that the amount of time and calculations needed to generate library 185 can be reduced.

In some applications, multiple blocks of hypothetical layers 404 can be used to characterize a hypothetical profile. For example, with reference to FIG. 6A, profile 300A can be characterized by blocks of hypothetical layers 404.1, 404.2, and 404.3. In the present embodiment, an error minimization algorithm can be utilized to determine the appropriate blocks of hypothetical layers 404 to use in characterizing profile 300A.

In the present example, for profile 300A, the diffraction calculations associated with blocks of hypothetical layers 404.1, 404.2, and 404.3 are retrieved from cache 406. Boundary conditions are then applied to generate the simulated-diffraction signal for profile 300A. More particularly, the boundary conditions at the top and bottom of profile 300A are applied. The resulting simulated-diffraction signal and profile 300A are then stored in library 185.

As described above, the parameters that define hypothetical profile 300A can be varied to define another profile. In this example, with reference to FIG. 6B, assume that the parameters are varied to define hypothetical profile 300B.

Figure 6B:
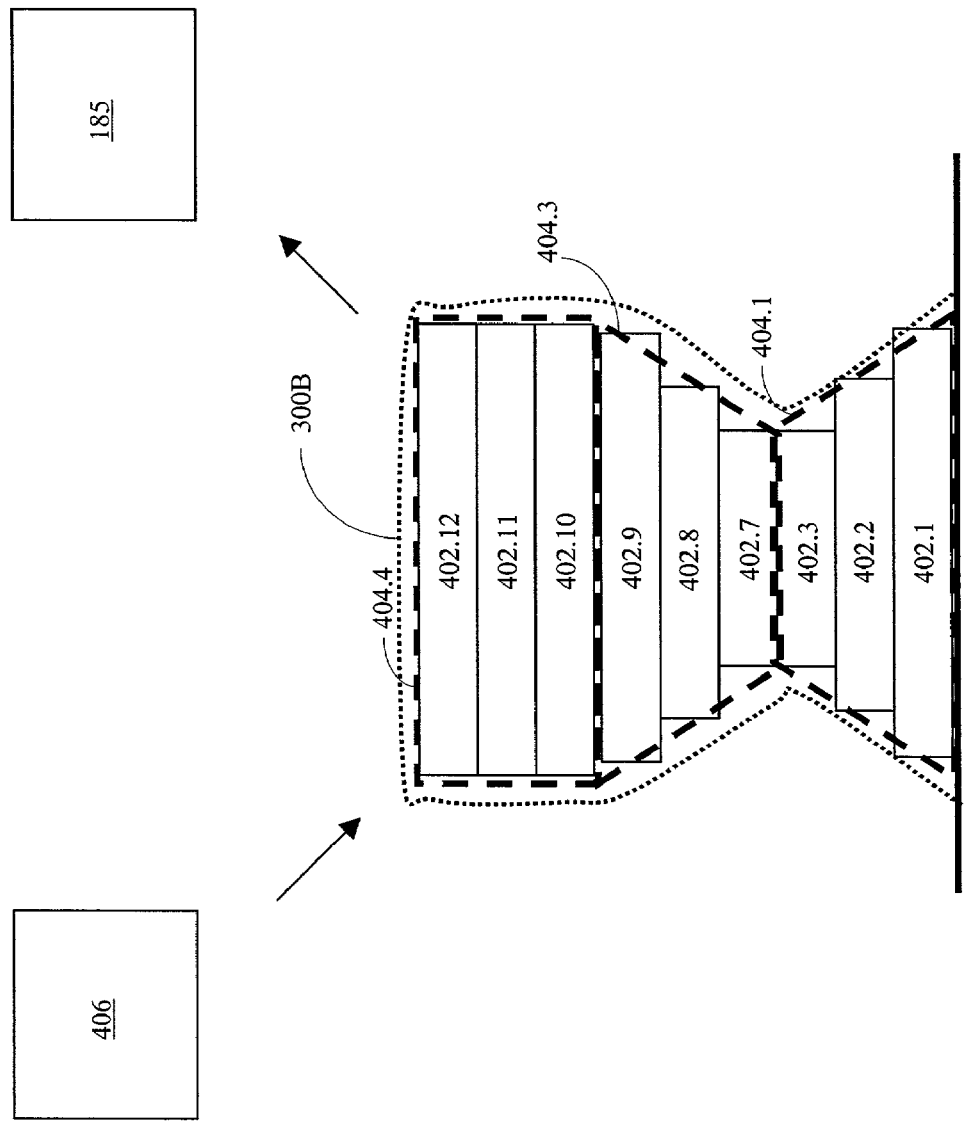

As depicted in FIG. 6B, hypothetical profile 300B can be characterized by blocks of hypothetical layers 404.1, 404.3, and 404.4. As such, the diffraction calculations associated with blocks of hypothetical layers 404.1, 404.3, and 404.4 are retrieved from cache 406. Boundary conditions are then applied to generate the simulated-diffraction signal for hypothetical profile 300B. The resulting simulated-diffraction signal and hypothetical profile 300B are then stored in library 185.

Figure 7A:
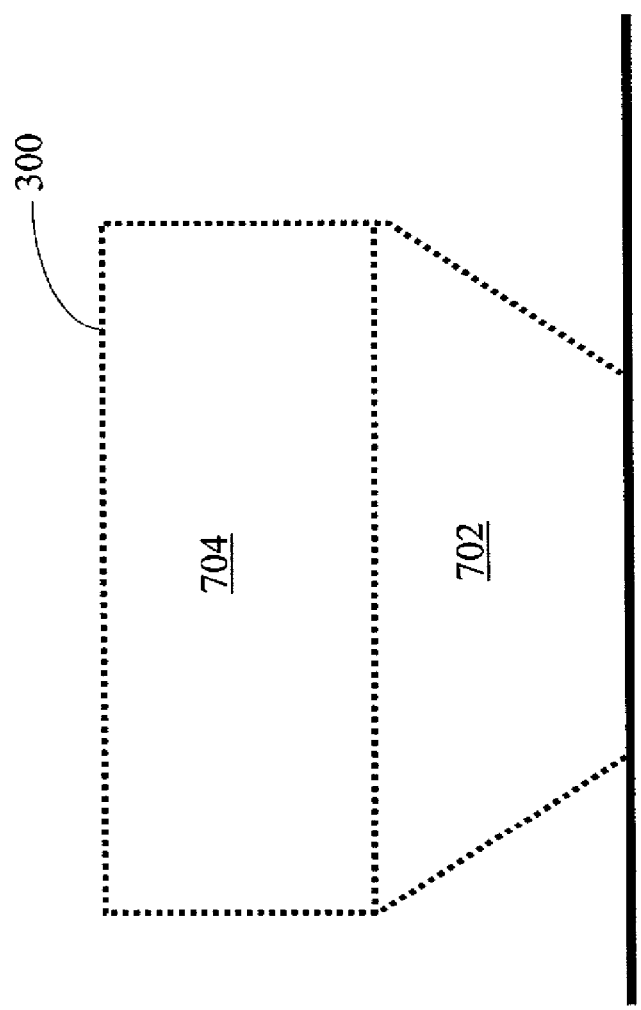
FIGS. 7A and 7B depict still another exemplary process of generating simulated-diffraction signals.

In some applications, a hypothetical profile can include multiple materials. For example, with reference to FIG. 7A, assume that hypothetical profile 300 is used to characterize an actual profile of a grating periodic formed from two materials. More particularly, as depicted in FIG. 7A, hypothetical profile 300 includes a first layer 702 and a second layer 704. In the present example, assume that first layer 702 represents an oxide layer of the actual profile, and second layer 704 represents a metal layer of the actual profile. Note that hypothetical profile 300 can include any number of layers to represent layers of any number of materials in an actual profile.

Figure 7B:
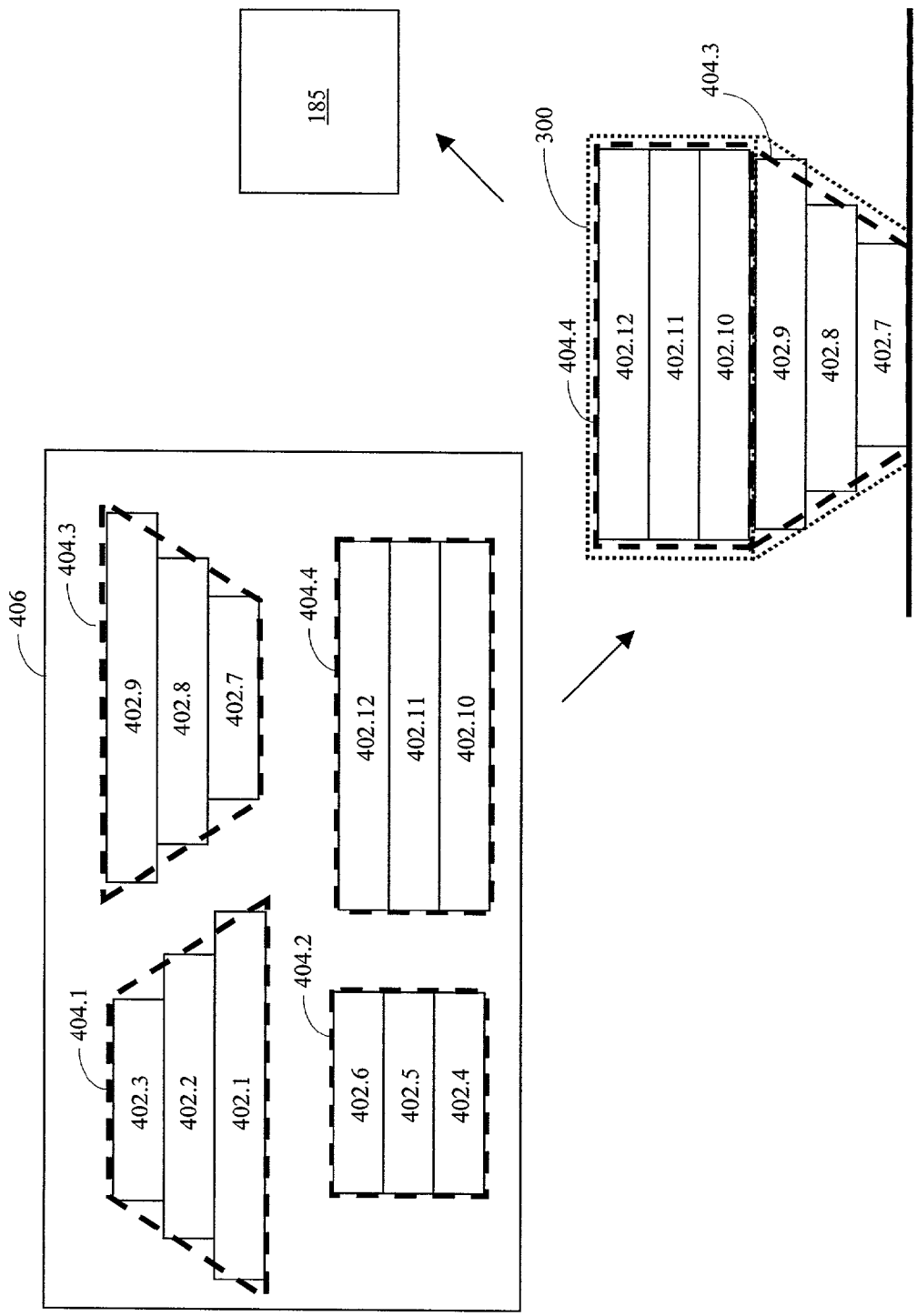

With reference to FIG. 7B, in the present example, assume that cache 406 includes blocks of hypothetical layers 404 of various materials as well as various shapes. For example, assume that blocks of hypothetical profiles 404.1 and 404.3 represent oxide layers, and hypothetical profiles 404.2 and 404.4 represent metal layers. As such, as depicted in FIG. 7B, profile 300 can be characterized by blocks of hypothetical layers 404.3 and 404.4 from cache 406. Boundary conditions are then applied to generate the simulated-diffraction signal for profile 300. The simulated-diffraction signal and profile 300 are then stored in library 185.

Thus far, hypothetical layers 402 and blocks of hypothetical layers 404 have been depicted as having rectangular and trapezoidal shapes, respectively. As will be described in greater detail below, the diffraction calculation for a hypothetical layer 402 depends on its width but not on its height. However, the diffraction calculation for a block of hypothetical layers 404 depends on its height as well as its width. Therefore, the blocks of hypothetical layers 404 stored in cache 406 are characterized and indexed, in part, by their width and their height. More particularly, when blocks of hypothetical layers 404 have symmetric-trapezoidal shapes, they can be indexed by their height, bottom width (bottom CD), and top width (top CD). However, as noted earlier, blocks of hypothetical layers 404 can have various shapes. As such, they can be characterized and indexed using any number of parameters.

Figure 8:
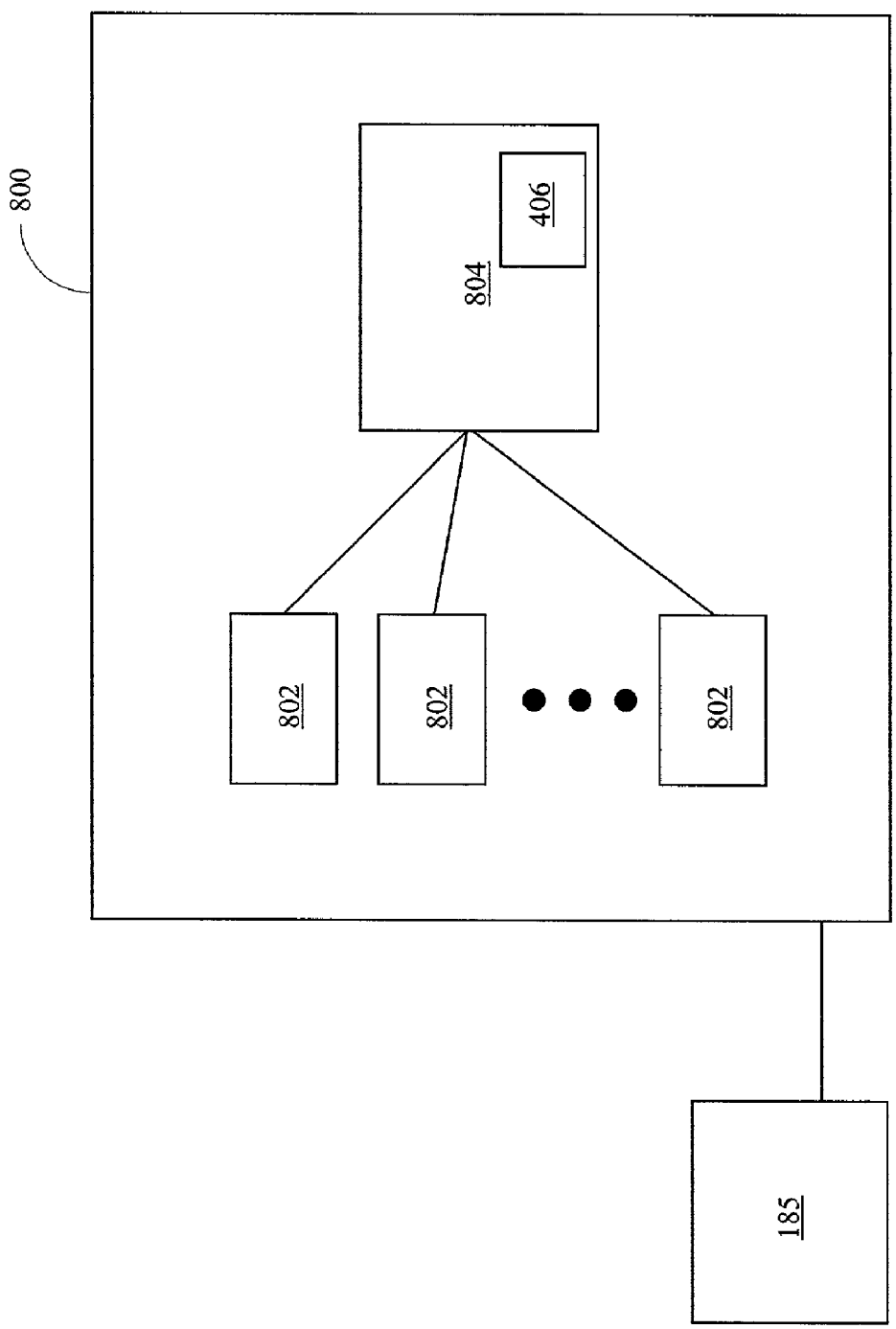
FIG. 8 depicts an exemplary computer system.

With reference to FIG. 8, in one exemplary embodiment, library 185 can be generated using computer system 800. As noted above and as will be described in greater detail below, the process of generating library 185 can involve performing a large number of complex calculations.

For example, assume that a set of hypothetical profiles is to be generated for a periodic grating that is to have a profile with a bottom CD of 200 nm. Assume that a 10% process variation is expected for the bottom CD of the periodic grating, which means that the bottom CD is expected to vary between about 180 to about 220 nm. Also assume that the top CD is expected to vary between about 160 to about 180 nm. Assume that the nominal thickness (i.e., the height) of the periodic grating is to be about 500 nm, and that a 10% process variation is expected, which means that the height can vary between about 450 to about 550 nm. Now assume that the desired resolution is 1 nm, which means that each parameter of the hypothetical profiles is varied by an increment of 1 nm.

In generating the set of hypothetical profiles, the top CD of the hypothetical profiles is varied between 160 to 180 nm in steps of 1 nm. The bottom CD of the hypothetical profiles is varied between 180 to 220 nm in steps of 1 nm. The thickness/height of the hypothetical profiles is varied between 450 to 550 nm in steps of 1 nm. Thus, in this example, a total of 87,000 hypothetical profiles (i.e., 21 variations of the top CD multiplied by 41 variations of the bottom CD multiplied by 101 variations of the thickness/height).

Now, assume that diffraction calculations are to be generated for each hypothetical profile at 53 different wavelengths. Also assume that each diffraction calculation uses 6 matrices with 9 orders and 8 bytes, which totals 17 kbytes.

As such, in this example, to store the diffraction calculations for all of the 87,000 hypothetical profiles at 53 different wavelengths, a total of 78 Gigabytes is needed.

As such, computer system 800 can include multiple processors 802 configured to perform portions of the computations in parallel. However, computer system 800 can be configured with a single processor 802.

Additionally, computer system 800 can include a memory 804 configured with a large amount of memory, such as 8 Gigabytes, 16 Gigabytes, 32 Gigabytes, and the like, that can be accessed by the multiple processors 802. It should be recognized, however, computer system 800 can be configured with any number and size of memories 804.

In one exemplary embodiment, as depicted in FIG. 8, cache 406 can reside in memory 804. As such, the blocks of hypothetical layers and hypothetical profiles stored in cache 406 can be more quickly accessed by computer system 800, and more particularly processors 802, than if cache 406 resided on a hard drive.

Additionally, in one exemplary embodiment, library 185 can reside on various computer-readable storage media. For example, library 185 can reside on a compact disk that is written to by computer system 800 when library 185 is generated, and read by signal processing module 190 (FIG. 1) when library 185 is used to determine the profile of periodic grating 145 (FIG. 1) on wafer 140 (FIG. 1).

3. Rigorous Coupled-Wave Analysis for Incident Radiation

As described above, simulated-diffraction signals are generated for hypothetical profiles based on diffraction calculation generated for hypothetical layers 402 and blocks of hypothetical layers 404. As will be described below, in one exemplary embodiment, simulated-diffraction signals and diffraction calculations can be generated by applying Maxwell's equations and using a numerical analysis technique to solve Maxwell's equations. More particularly, in the exemplary embodiment described below, rigorous coupled-wave analysis is used. It should be noted, however, that various numerical analysis techniques, including variations of the rigorous coupled-wave analysis technique described below, can be used.

Figure 9:
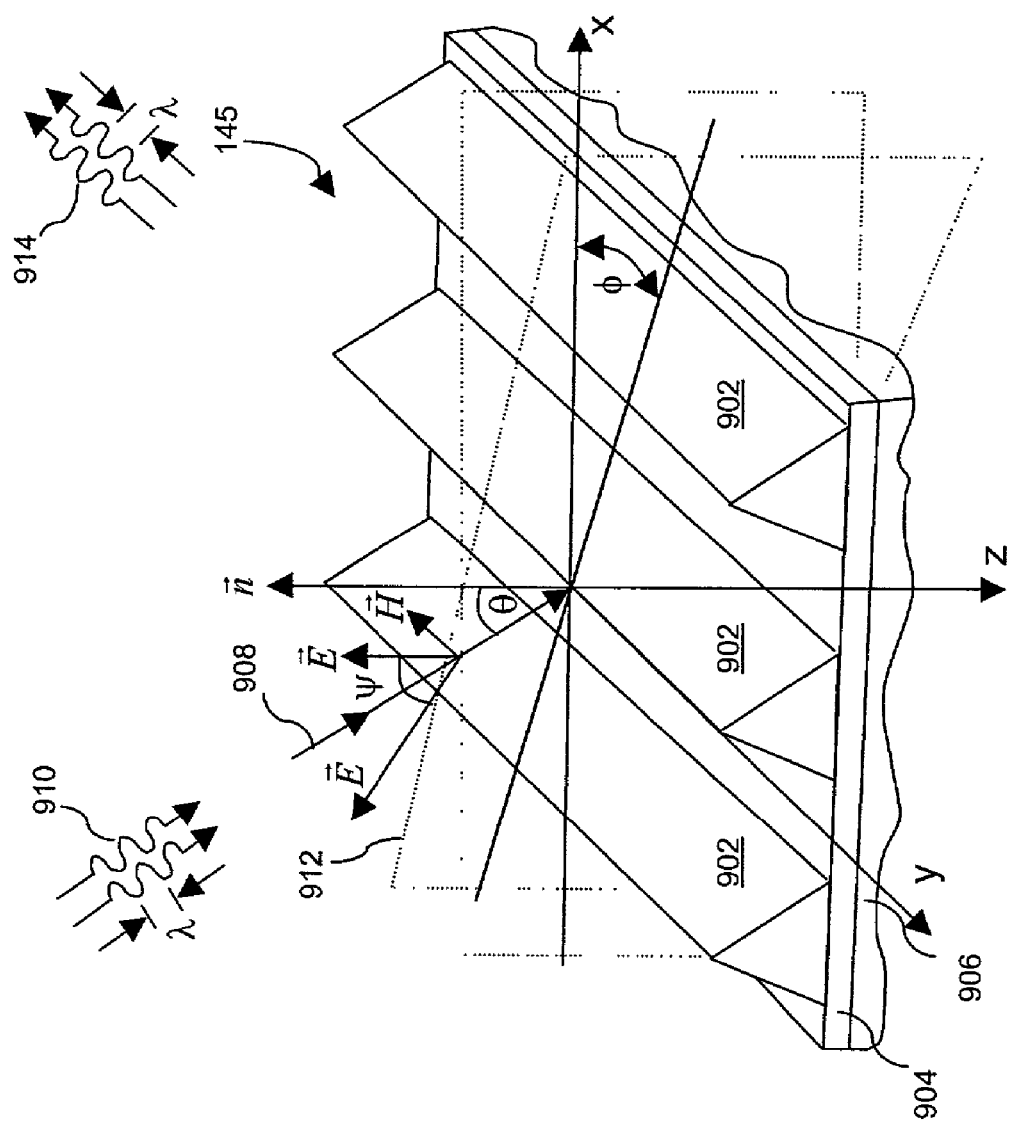
FIG. 9 shows a section of a periodic grating.

With reference to FIG. 9, a section of periodic grating 145 is shown. In FIG. 9, the section of the grating 145 is depicted as having three ridges 902, which have a triangular cross-section. It should be noted that ridges can have shapes that are considerably more complex, and the categories of "ridges" and "troughs" may be ill-defined. For the sake of convenience and clarity, the term "ridge" will be used hereafter to refer to one period of a periodic structure on a substrate. Each ridge 902 is considered to extend infinitely in the +y and −y directions, and an infinite, regularly-spaced series of such ridges 902 are considered to extend in the +x and −x directions. The ridges 902 are atop a deposited film 904, and the film 904 is atop a substrate 906, which is considered to extend semi-infinitely in the +z direction. The normal vector n to the grating is in the −z direction.

FIG. 9 illustrates the variables associated with a mathematical analysis of a diffraction grating according to the present exemplary embodiment. In particular:

θ is the angle between the Poynting vector 908 of the incident electromagnetic radiation 910 and the normal vector n of the grating 145. The Poynting vector 908 and the normal vector n define the plane of incidence 912.

φ is the azimuthal angle of the incident electromagnetic radiation 910, i.e., the angle between the direction of periodicity of the grating, which in FIG. 9 is along the x axis, and the plane of incidence 912. For ease of presentation, in the mathematical analysis of the present specification the azimuthal angle φ is set to zero.

ψ is the angle between the electric-field vector $\vec{E}$ of the incident electromagnetic radiation 910 and the plane of incidence 912, i.e., between the electric field vector $\vec{E}$ and its projection $\vec{E}'$ on the plane of incidence 912. When φ=0 and the incident electromagnetic radiation 910 is polarized so that ψ=π/2, the electric-field vector $\vec{E}$ is perpendicular to the plane of incidence 912 and the magnetic-field vector $\vec{H}$ lies in the plane of incidence 912, and this is referred to as the TE polarization. When φ=0 and the incident electromagnetic radiation 910 is polarized so that ψ=0, the magnetic-field vector $\vec{H}$ is perpendicular to the plane of incidence 912 and the electric-field vector $\vec{E}$ lies in the plane of incidence 912, and this is referred to as the TM polarization. Any planar polarization is a combination of in-phase TE and TM polarizations. The method of the present invention described below can be applied to any polarization that is a superposition of TE and TM polarizations by computing the diffraction of the TE and TM components separately and summing them. Furthermore, although the 'off-axis' φ≠0 case is more complex because it cannot be separated into TE and TM components, the present invention is applicable to off-axis incidence radiation as well.

λ is the wavelength of the incident electromagnetic radiation 910.

Figure 10A:
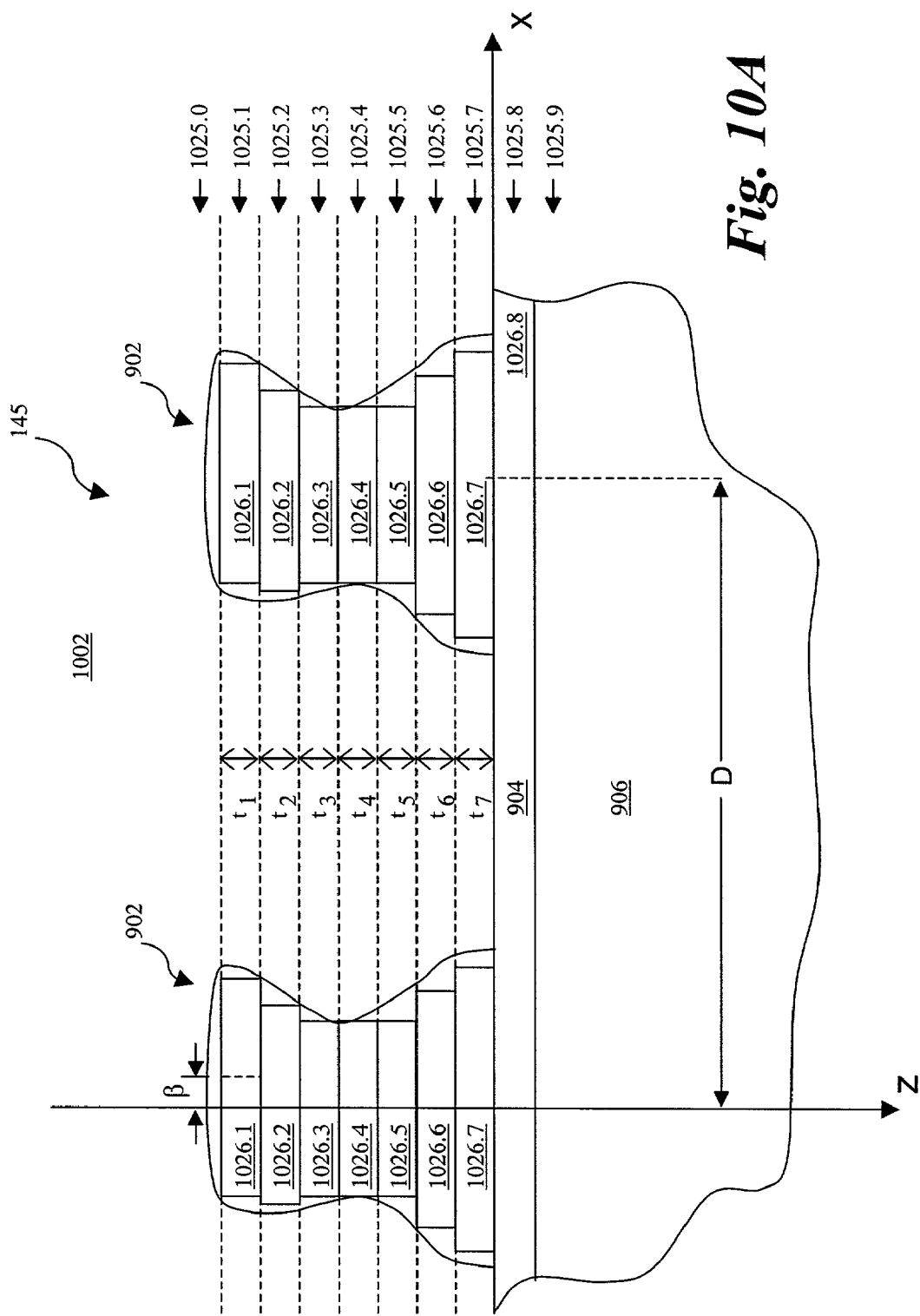

FIG. 10A shows a cross-sectional view of two ridges 902 of periodic grating 145 illustrating the variables associated with a mathematical description of the dimensions of the diffraction grating 145. In particular:

L is the number of the layers into which the system is divided. Layers 0 and L are considered to be semi-infinite layers. Layer 0 is an "atmospheric" layer 1002, such as vacuum or air, which typically has a refractive index $n_0$ of unity. Layer L is a "substrate" layer 906, which is typically silicon or germanium in semiconductor applications. In the case of the exemplary grating 145 of FIG. 10A, the grating 145 has ten layers with the atmospheric layer 1002 being the zeroeth layer 1025.0, the ridges 902 being in the first through seventh layers 1025.1 through 1025.7, the thin film 904 being the eighth layer 1025.8, and the substrate 906 being the ninth layer 1025.9. For the mathematical analysis described below, the thin-film 904 is considered as a periodic portion of the ridge 902 with a width d equal to the pitch D. The portion of ridge 902 within each intermediate layer 1025.1 through 1025.(L−1) is approximated by a thin planar slab 1026 having a rectangular cross-section. Generically or collectively, the layers are assigned reference numeral 1025, and, depending on context, "layers 1025" may be considered to include the atmospheric layer 1002 and/or the substrate 906. In general, any geometry of ridges 902 with a cross-section which does not consist solely of vertical and horizontal sections can be better approximated using a large number of layers 1025.

D is the periodicity length or pitch, i.e., the length between equivalent points on pairs of adjacent ridges 902.

$d_l$ is the width of the rectangular ridge slab 1026.l in the lth layer 1025.l.

$t_l$ is the thickness of the rectangular ridge slab 1026.l in the lth layer 1025.l for $1<l<(L-1)$. The thicknesses $t_l$ of the layers 1025 are chosen such that every vertical line segment within a layer 1025 passes through only a single material. For instance, if in FIG. 10 the materials in layers 1025.4, 1025.5, and 1025.6 are the same, but different than the materials in layers 1025.3 and 1025.7, than it would be acceptable to combine layers 1025.4 and 1025.5, or layers 1025.5 and 1025.6, or layers 1025.4, 1025.5 and 1025.6 into a single layer. However, it would not be acceptable to combine layers 1025.3 and 1025.4, or layers 1025.6 and 1025.7 into a single layer.

$n_l$ is the index of refraction of the material in the rectangular ridge slab 1026 of the lth layer 1025.l.

In determining the diffraction generated by grating 145, a Fourier space version of Maxwell's equations is used. As shown in the calculation process flow diagram of FIG. 11, the permittivities $\epsilon_l(x)$ for each layer l are determined or acquired (1110), and a one-dimensional Fourier transformation of the permittivity $\epsilon_l(x)$ of each layer l is performed (1112) along the direction of periodicity, $\hat{x}$, of the periodic grating 145 to provide the harmonic components of the permittivity $\epsilon_{l,i}$, where i is the order of the harmonic component. In FIGS. 11, 12, 13, and 14 process steps are shown enclosed within ovals or rectangles with rounded corners, and the results of calculations are shown enclosed within rectangles with sharp corners. When appropriate in FIG. 11, equation numbers are used in lieu of, or in addition to, reference numerals. In particular, the real-space permittivity $\epsilon_l(x)$ of the lth layer is related to the permittivity harmonics $\epsilon_{l,i}$ of the lth layer by $$\epsilon_l(x) = \sum_{i=-\infty}^{\infty} \epsilon_{l,i} \exp\left(j\frac{2\pi i}{D}x\right). \quad (1.1.1)$$

Therefore, via the inverse transform, $$\epsilon_{l,0} = n_r^2 \frac{d_l}{D} + n_0^2 \left(1 - \frac{d_l}{D}\right), \quad (1.1.2)$$

and for i not equal to zero, $$\epsilon_{l,i} = (n_r^2 - n_0^2) \frac{\sin\left(\pi i \frac{d_l}{D}\right)}{\pi i} e^{-j\pi\beta/D}, \quad (1.1.3)$$

where $n_r$ is the index of refraction of the material in the ridges 902 in layer l, the index of refraction $n_o$ of the atmospheric layer 1002 is typically near unity, and $\beta$ is the x-offset of the center of the central rectangular ridge slab 1026.l (i.e., the ridge 902 nearest x=0, where generally it is attempted to position the x=0 point at the center of a ridge 902) from the origin. The present specification explicitly addresses periodic gratings where a single ridge material and a single atmospheric material are found along any line in the x-direction. However, gratings can have more than one ridge material along a line in the x-direction.

In the present embodiment, it is convenient to define the $(2o+1)\times(2o+1)$ Toeplitz-form, permittivity harmonics matrix $E_l$ as $$E_l = \begin{bmatrix} \epsilon_{l,0} & \epsilon_{l,-1} & \epsilon_{l,-2} & \cdots & \epsilon_{l,-2o} \\ \epsilon_{l,1} & \epsilon_{l,0} & \epsilon_{l,-1} & \cdots & \epsilon_{l,-(2o-1)} \\ \epsilon_{l,2} & \epsilon_{l,1} & \epsilon_{l,0} & \cdots & \epsilon_{l,-(2o-2)} \\ \cdots & \cdots & \cdots & \cdots & \cdots \\ \epsilon_{l,2o} & \epsilon_{l,(2o-1)} & \epsilon_{l,(2o-2)} & \cdots & \epsilon_{l,0} \end{bmatrix}. \quad (1.1.4)$$

As will be seen below, to perform a TE-polarization calculation where oth-order harmonic components of the electric field $\vec{E}$ and magnetic field $\vec{H}$ are used, it is necessary to use harmonics of the permittivity $\epsilon_{l,i}$ up to order 2o.

For the TE polarization, in the atmospheric layer the electric field $\vec{E}$ is formulated (1124) as $$\vec{E}_{0,y} = \exp(-jk_0 n_0(\sin\theta x + \cos\theta z)) + \sum_i R_i \exp(-j(k_{xi}x - k_{0,zi}z)), \quad (1.2.1)$$

where the term on the left of the right-hand side of equation (1.2.1) is an incoming plane wave at an angle of incidence $\theta$, the term on the right of the right-hand side of equation (1.2.1) is a sum of reflected plane waves and $R_i$ is the magnitude of the ith component of the reflected wave, and the wave vectors $k_o$ and $(k_{xi}, k_{0,zi})$ are given by $$k_0 = \frac{2\pi}{\lambda} = \omega(\mu_0\epsilon_0)^{\frac{1}{2}}, \quad (1.2.2)$$

$$k_{xi} = k_0\left(n_0\sin(\theta) - i\left(\frac{\lambda}{D}\right)\right), \quad (1.2.3)$$

and $$k_{0,zi} = \begin{cases} k_0(n_l^2 - (k_{xi}/k_0)^2)^{\frac{1}{2}} \\ -jk_0(n_l^2 - (k_{xi}/k_0)^2)^{\frac{1}{2}}. \end{cases} \quad (1.2.4)$$

where the value of $k_{0,zi}$ is chosen from equation (1.2.4), i.e., from the top or the bottom of the expression, to provide $\text{Re}(k_{0,zi})-\text{Im}(k_{0,zi})>0$. This insures that $k_{0,zi}^2$ has a positive real part, so that energy is conserved. It is easily confirmed that in the atmospheric layer 1002, the reflected wave vector $(k_{xi}, k_{0,zi})$ has a magnitude equal to that of the incoming wave vector $k_0 n_0$. The magnetic field $\vec{H}$ in the atmospheric layer 1002 is generated from the electric field $\vec{E}$ by Maxwell's equation (1.3.1) provided below.

The x-components $k_{xi}$ of the outgoing wave vectors satisfy the Floquet condition (which is also called Bloch's Theorem, see Solid State Physics, N. W. Ashcroft and N. D. Mermin, Saunders College, Philadelphia, 1976, pages 133–134) in each of the layers 1025 containing the periodic ridges 902, and therefore, due to the boundary conditions, in the atmospheric layer 1002 and the substrate layer 906 as well. That is, for a system having an n-dimensional periodicity given by $$f(\vec{r}) = f\left(\vec{r} + \sum_{i=1}^{n} m_i \vec{d}_i\right), \quad (1.2.5)$$

where $\vec{d}_i$ are the basis vectors of the periodic system, and $m_i$ takes on positive and negative integer values, the Floquet condition requires that the wave vectors $\vec{k}$ satisfy $$\vec{k} = \vec{k}_0 + 2\pi \sum_{i=1}^{n} m_i \vec{b}_i, \quad (1.2.6)$$

where $\vec{b}_i$ are the reciprocal lattice vectors given by $$(\vec{b}_i \cdot \vec{d}_j) = \delta_{ij}, \quad (1.2.7)$$

$\vec{k}_0$ is the wave vector of a free-space solution, and $\delta_{ij}$ the Kronecker delta function. In the case of the layers 1025 of the periodic grating 145 of FIGS. 9 and 10, which have the single reciprocal lattice vector $\vec{b}$ is $\hat{x}/D$, thereby providing the relationship of equation (1.2.3).

It may be noted that the formulation given above for the electric field in the atmospheric layer 1002, although it is an expansion in terms of plane waves, is not determined via a Fourier transform of a real-space formulation. Rather, the formulation is produced (1124) a priori based on the Floquet condition and the requirements that both the incoming and outgoing radiation have wave vectors of magnitude $n_0 k_0$. Similarly, the plane wave expansion for the electric field in the substrate layer 906 is produced (1124) a priori. In the substrate layer 906, the electric field $\vec{E}$ is formulated (1124) as a transmitted wave which is a sum of plane waves where the x-components $k_{xi}$ of the wave vectors $(k_{xi}, k_{0,zi})$ satisfy the Floquet condition, i.e., $$\vec{E}_{L,y} = \sum_i T_i \exp\left(-j\left(k_{xi}x + k_{L,zi}\left(z - \sum_{l=1}^{L-1} t_l\right)\right)\right), \quad (1.2.8)$$

where $$k_{L,zi} = \begin{cases} k_0(n_L^2 - (k_{xi}/k_0)^2)^{\frac{1}{2}} \\ -jk_0(n_L^2 - (k_{xi}/k_0)^2)^{\frac{1}{2}}. \end{cases} \quad (1.2.9)$$

where the value of $k_{L,zi}$ is chosen from equation (1.2.9), i.e., from the top or the bottom of the expression, to provide $\text{Re}(k_{L,zi}) - \text{Im}(k_{L,zi}) > 0$, insuring that energy is conserved.

The plane wave expansions for the electric and magnetic fields in the intermediate layers 1025.1 through 1025.(L−1) are also produced (1134) a priori based on the Floquet condition. The electric field $\vec{E}_{l,y}$ in the lth layer is formulated (1134) as a plane wave expansion along the direction of periodicity, $\hat{x}$, i.e., $$\vec{E}_{l,y} = \sum_i S_{l,yi}(z) \exp(-jk_{xi}x), \quad (1.2.10)$$

where $S_{l,yi}(z)$ is the z-dependent electric field harmonic amplitude for the lth layer and the ith harmonic. Similarly, the magnetic field $\vec{H}_{l,y}$ in the lth layer is formulated (1134) as a plane wave expansion along the direction of periodicity, $\hat{x}$, i.e., $$\vec{H}_{l,x} = -j\left(\frac{\varepsilon_0}{\mu_0}\right)^{\frac{1}{2}} \sum_i U_{l,xi}(z) \exp(-jk_{xi}x), \quad (1.2.11)$$

where $U_{l,xi}(z)$ is the z-dependent magnetic field harmonic amplitude for the lth layer and the ith harmonic.

According to Maxwell's equations, the electric and magnetic fields within a layer are related by $$\vec{H}_l = \left(\frac{j}{\omega\mu_0}\right)\nabla \times \vec{E}_l, \quad (1.3.1)$$

and $$\vec{E}_l = \left(\frac{-j}{\omega\varepsilon_0\varepsilon_l(x)}\right)\nabla \times \vec{H}_l. \quad (1.3.2)$$

Applying (1142) the first Maxwell's equation (1.3.1) to equations (1.2.10) and (1.2.11) provides a first relationship between the electric and magnetic field harmonic amplitudes $S_l$ and $U_l$ of the lth layer:

$$\frac{\partial S_{l,yi}(z)}{\partial z} = k_0 U_{l,xi}. \quad (1.3.3)$$

Similarly, applying (1141) the second Maxwell's equation (1.3.2) to equations (1.2.10) and (1.2.11), and taking advantage of the relationship $$k_{xi} + \frac{2\pi h}{D} = k_{x(i-h)} \quad (1.3.4)$$

which follows from equation (1.2.3), provides a second relationship between the electric and magnetic field harmonic amplitudes $S_l$ and $U_l$ for the lth layer:

$$\frac{\partial U_{l,xi}}{\partial z} = \left(\frac{k_{xi}^2}{k_0}\right) S_{l,yi} - k_0 \sum_p \varepsilon_{(i-p)} S_{l,yp}. \quad (1.3.5)$$

While equation (1.3.3) only couples harmonic amplitudes of the same order i, equation (1.3.5) couples harmonic amplitudes $S_l$ and $U_l$ between harmonic orders. In equation (1.3.5), permittivity harmonics $\varepsilon_i$ from order −2o to +2o are required to couple harmonic amplitudes $S_l$ and $U_l$ of orders between −o and +o.

Combining equations (1.3.3) and (1.3.5) and truncating the calculation to order o in the harmonic amplitude S provides (1145) a second-order differential matrix equation having the form of a wave equation, i.e., $$\left[\frac{\partial^2 S_{l,y}}{\partial z'^2}\right] = [A_l][S_{l,y}], \quad (1.3.6)$$

$z' = k_0 z$, the wave-vector matrix $[A_l]$ is defined as $$[A_l] = [K_x]^2 - [E_l], \quad (1.3.7)$$

where $[K_x]$ is a diagonal matrix with the (i,i) element being equal to $(k_{xi}/k_0)$, the permittivity harmonics matrix $[E_l]$ is defined above in equation (1.1.4), and $[S_{l,y}]$ and $[\partial^2 S_{l,y}/\partial z'^2]$ are column vectors with indices i running from $-o$ to $+o$, i.e., $$[S_{l,y}] = \begin{bmatrix} S_{l,y,(-o)} \\ \vdots \\ S_{l,y,0} \\ \vdots \\ S_{l,y,o} \end{bmatrix}, \quad (1.3.8)$$

By writing (1150) the homogeneous solution of equation (1.3.6) as an expansion in pairs of exponentials, i.e., $$S_{l,yi}(z) = \sum_{m=1}^{2o+1} w_{l,i,m}[c1_{l,m}\exp(-k_0 q_{l,m} z) + c2_{l,m}\exp(k_0 q_{l,m}(z - t_l))], \quad (1.3.9)$$

its functional form is maintained upon second-order differentiation by $z'$, thereby taking the form of an eigenequation. Solution (1147) of the eigenequation $$[A_l][W_l] = [\tau_l][W_l] \quad (1.3.10)$$

provides (1148) a diagonal eigenvalue matrix $[\tau_l]$ formed from the eigenvalues $\sigma_{l,m}$ of the wave-vector matrix $[A_l]$, and an eigenvector matrix $[W_l]$ of entries $w_{l,i,m}$, where $w_{l,i,m}$ is the ith entry of the mth eigenvector of $[A_l]$. A diagonal root-eigenvalue matrix $[Q_l]$ is defined to be diagonal entries $q_{l,i}$ which are the positive real portion of the square roots of the eigenvalues $\sigma_{l,i}$. The coefficients c1 and c2 are, as yet, undetermined.

By applying equation (1.3.3) to equation (1.3.9) it is found that $$U_{l,xi}(z) = \sum_{m=1}^{2o+1} v_{l,i,m}[-c1_{l,m}\exp(-k_0 q_{l,m} z) + c2_{l,m}\exp(k_0 q_{l,m}(z - t_l))] \quad (1.3.11)$$

where $v_{l,i,m} = q_{l,m} w_{l,i,m}$. The matrix $[V_l]$, to be used below, is composed of entries $v_{l,i,m}$.

The coefficients c1 and c2 in the homogeneous solutions of equations (1.3.9) and (1.3.11) are determined by applying (1155) the requirement that the tangential electric and magnetic fields be continuous at the boundary between each pair of adjacent layers $1025.l/(1025.(l+1))$. At the boundary between the atmospheric layer 1002 and the first layer 1025.1, continuity of the electric field $E_y$ and the magnetic field $H_x$ requires $$\begin{bmatrix} \delta_{i0} \\ jn_0\cos(\theta)\delta_{i0} \end{bmatrix} + \begin{bmatrix} I \\ -jY_0 \end{bmatrix} R = \begin{bmatrix} W_1 & W_1 X_1 \\ V_1 & -V_1 X_1 \end{bmatrix} \begin{bmatrix} c1_1 \\ c2_1 \end{bmatrix} \quad (1.4.1)$$

where $Y_0$ is a diagonal matrix with entries $(k_{0,zi}/k_0)$, $X_l$ is a diagonal layer-translation matrix with elements $\exp(-k_0 q_{l,m} t_l)$, R is a vector consisting of entries from $R_{-o}$ to $R_{+o}$ and $c1_l$ and $c2_l$ are vectors consisting of entries from $c1_{l,0}$ to $c1_{l,2o+1}$, and $c2_{l,0}$ to $c2_{l,2o+1}$, respectively. The top half of matrix equation (1.4.1) provides matching of the electric field $E_y$ across the boundary of the atmospheric layer 1025.0 and the first layer 1025.1, the bottom half of matrix equation (1.4.1) provides matching of the magnetic field $H_x$ across the layer boundary 1025.0/1025.1, the vector on the far left is the contribution from the incoming radiation 910 in the atmospheric layer 1002, the second vector on the left is the contribution from the reflected radiation 914 in the atmospheric layer 1002, and the portion on the right represents the fields $E_y$ and $H_x$ in the first layer 1025.1.

At the boundary between adjacent intermediate layers 1025.l and 1025.(l+1), continuity of the electric field $E_y$ and the magnetic field $H_x$ requires $$\begin{bmatrix} W_{l-1} X_{l-1} & W_{l-1} \\ V_{l-1} X_{l-1} & -V_{l-1} \end{bmatrix} \begin{bmatrix} c1_{l-1} \\ c2_{l-1} \end{bmatrix} = \begin{bmatrix} W_l & W_l X_l \\ V_l & -V_l X_l \end{bmatrix} \begin{bmatrix} c1_l \\ c2_l \end{bmatrix}, \quad (1.4.2)$$

where the top and bottom halves of the vector equation provide matching of the electric field $E_y$ and the magnetic field $H_x$, respectively, across the l-1/l layer boundary.

At the boundary between the (L-1)th layer 1025.(L-1) and the substrate layer 906, continuity of the electric field $E_y$ and the magnetic field $H_x$ requires $$\begin{bmatrix} W_{L-1} X_{L-1} & W_{L-1} \\ V_{L-1} X_{L-1} & -V_{L-1} \end{bmatrix} \begin{bmatrix} c1_{L-1} \\ c2_{L-1} \end{bmatrix} = \begin{bmatrix} I \\ jY_L \end{bmatrix} T, \quad (1.4.3)$$

where, as above, the top and bottom halves of the vector equation provides matching of the electric field $E_y$ and the magnetic field $H_x$, respectively. In contrast with equation (1.4.1), there is only a single term on the right since there is no incident radiation in the substrate 906.

Figure 12:
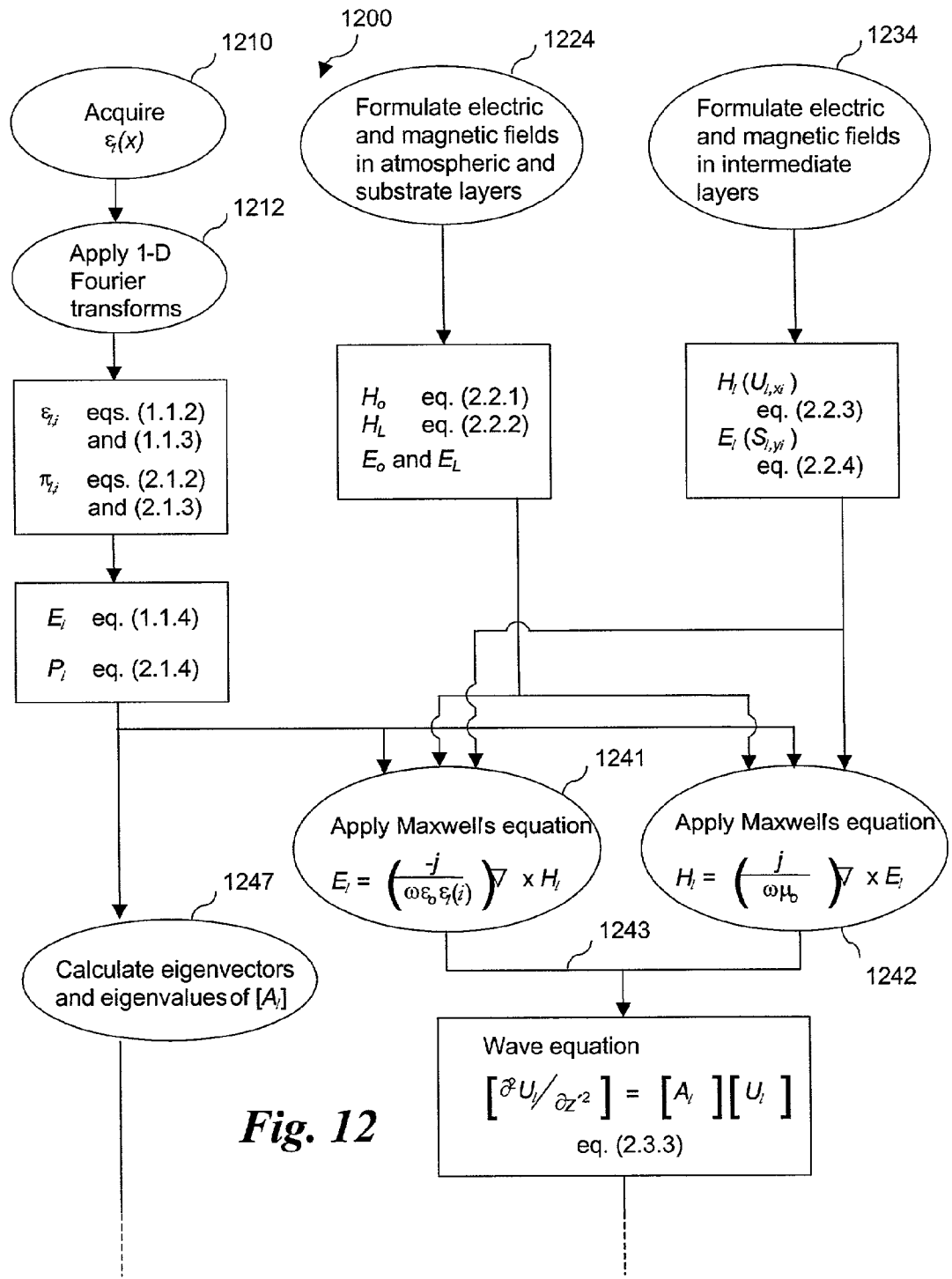
FIG. 12 depicts another exemplary coupled-wave analysis.
Figure 12:
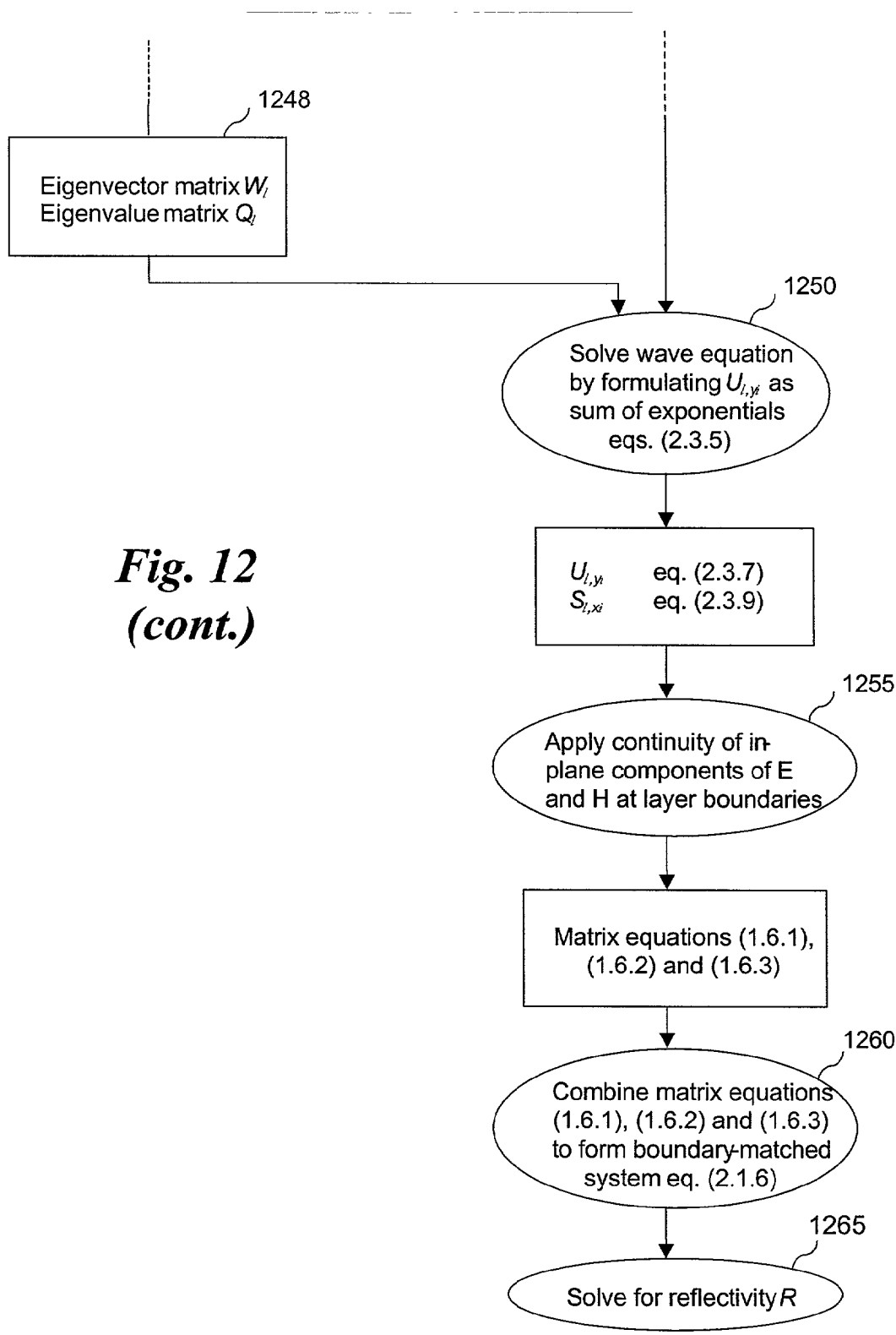

The method (1200) of calculation for the diffracted reflectivity of TM-polarized incident electromagnetic radiation 910 shown in FIG. 12 parallels the method (1100) described above and shown in FIG. 11 for the diffracted reflectivity of TE-polarized incident electromagnetic radiation 910. The variables describing the geometry of the grating 145 and the geometry of the incident radiation 910 are as shown in FIGS. 9 and 10A. However, for TM-polarized incident radiation 910 the electric field vector $\vec{E}$ is in the plane of incidence 912, and the magnetic field vector $\vec{H}$ is perpendicular to the plane of incidence 912. The similarity in the TE- and TM-polarization RCWA calculations, in part, motivates the use of the term "electromagnetic field" in the present specification to refer generically to either or both the electric field and/or the magnetic field of the electromagnetic radiation.

The most substantial difference between the calculation (1200) for TE-polarized incident electromagnetic radiation 910 and the calculation (1100) for TM-polarized incident electromagnetic radiation 910 is that for TM-polarized incident radiation the wave-vector matrix $[A_l]$ may be defined according to any of three formulations:

$$[A_l]=[E_l]([K_x][P_l][K_x]-[I]), \quad (1.5.1)$$

or $$[A_l]=[P_l]^{-1}([K_x][E_l]^{-1}[K_x]-[I]), \quad (1.5.2)$$

or $$[A_l]=[E_l]([K_x][E_l]^{-1}[K_x]-[I]). \quad (1.5.3)$$

In the above equations, the inverse-permittivity harmonics matrix $P_l$ is defined as $$P_l = \begin{bmatrix} \pi_{l,0} & \pi_{l,-1} & \pi_{l,-2} & \cdots & \pi_{l,-2o} \\ \pi_{l,1} & \pi_{l,0} & \pi_{l,-1} & \cdots & \pi_{l,-(2o-1)} \\ \pi_{l,2} & \pi_{l,1} & \pi_{l,0} & \cdots & \pi_{l,-(2o-2)} \\ \cdots & \cdots & \cdots & \cdots & \cdots \\ \pi_{l,2o} & \pi_{l,(2o-1)} & \pi_{l,(2o-2)} & \cdots & \pi_{l,0} \end{bmatrix}. \quad (1.5.4)$$

where $$\frac{1}{\varepsilon_l(x)} = \sum_{h=-\infty}^{\infty} \pi_{l,h} \exp\left(j\frac{2\pi h}{D}x\right), \quad (1.5.5)$$

so via the inverse Fourier transform, $$\pi_{l,0} = \frac{1}{n_r^2}\frac{d_l}{D} + \frac{1}{n_0^2}\left(1 - \frac{d_l}{D}\right), \quad (1.5.6)$$

and for h not equal to zero, $$\pi_{l,h} = \left(\frac{1}{n_r^2} - \frac{1}{n_0^2}\right) \frac{\sin\left(\pi h \frac{d_l}{D}\right)}{\pi h} e^{-j\pi h \beta / D}. \quad (1.5.7)$$

The fourth possible formulation for the wave-vector matrix $[A_l]$ $$[A_l]=[P_l]^{-1}([K_x][P_l][K_x]-[I]), \quad (1.5.8)$$

tends not to be computationally useful. Based on these definitions of the wave-vector matrix $[A_l]$, the matrix $[V_l]$ is defined as $$[V_l]=[E_l]^{-1}[W_l][Q_l] \quad (1.5.9)$$

when $[A]$ is defined as in equation (1.5.1), $$[V_l]=[P_l][W_l][Q_l] \quad (1.5.10)$$

when $[A]$ is defined as in equation (1.5.2), and $$[V_l]=[E_l]^{-1}[W_l][Q_l] \quad (1.5.11)$$

when $[A]$ is defined as in equation (1.5.3). The convergence of the RCWA calculation will vary depending on the formulation for the wave-vector matrix $[A_l]$, and the particulars of the grating 145 and the incident radiation 910.

Following through the calculation (1200) for TM-polarized incident electromagnetic radiation 910 paralleling the calculation (1100) described above for TE-polarized incident electromagnetic radiation 910, it is found that the reflectivity vector R is related to the coefficients $c1_1$ and $c2_1$ by $$\begin{bmatrix} \delta_{i0} \\ j\cos(\theta)\delta_{i0}/n_0 \end{bmatrix} + \begin{bmatrix} I \\ -jZ_0 \end{bmatrix} R = \begin{bmatrix} W_l & W_l X_l \\ V_l & -V_l X_l \end{bmatrix} \begin{bmatrix} c1_l \\ c2_l \end{bmatrix} \quad (1.6.1)$$

where $Z_0$ is a diagonal matrix with entries $(k_{0,zi}/n_0^2 k_0)$, and, as above, $X_l$ is the diagonal layer-translation matrix with elements $\exp(-k_0 q_{l,m} t_l)$. Similarly, following through the calculation (1200) for TM-polarized incident electromagnetic radiation 910 paralleling the calculation (1100) described above for TE-polarized incident electromagnetic radiation 910, it is found that the coefficients $c1_l$ and $c2_l$ are related to the coefficients $c1_{l-1}$ and $c2_{l-1}$ by $$\begin{bmatrix} W_{l-1}X_{l-1} & W_{l-1} \\ V_{l-1}X_{l-1} & -V_{l-1} \end{bmatrix} \begin{bmatrix} c1_{l-1} \\ c2_{l-1} \end{bmatrix} = \begin{bmatrix} W_l & W_l X_l \\ V_l & -V_l X_l \end{bmatrix} \begin{bmatrix} c1_l \\ c2_l \end{bmatrix}, \quad (1.6.2)$$

and the transmission vector T is related to the coefficients $c1_{L-1}$, and $c2_{L-1}$ by $$\begin{bmatrix} W_{L-1}X_{L-1} & W_{L-1} \\ V_{L-1}X_{L-1} & -V_{L-1} \end{bmatrix} \begin{bmatrix} c1_{L-1} \\ c2_{L-1} \end{bmatrix} = \begin{bmatrix} I \\ jZ_L \end{bmatrix} T. \quad (1.6.3)$$

Equation (1.6.1) only differs from equation (1.4.1) by the substitution of $Z_0$ for $Y_0$ and the replacement of $n_0$ with $1/n_0$ on the left side of the equation. Similarly, equation (1.6.3) only differs from equation (1.4.3) by the substitution of $Z_0$ for $Y_0$ on the right side of the equation. It is important to note that equation (1.6.2) is the same as equation (1.4.2), the right side of equation (1.6.1) is the same as the right side of equation (1.4.1), and the left side of equation (1.6.3) is the same as the left side of equation (1.4.3).

As disclosed in pending patent application Ser. No. 09/770,997, filed Jan. 25, 2001, entitled Caching of Intra-Layer Calculations for Rapid Rigorous Coupled-Wave Analyses, by the same inventors, and incorporated herein by reference, for TE-polarized incident electromagnetic radiation 910, matrix equation (1.4.1), matrix equation (1.4.3), and the (L-1) matrix equations (1.4.2) can be combined (1160) to provide the system matrix equation:

$$\begin{bmatrix} -I & W_1 & W_1X_1 & 0 & 0 & \cdots & & & \\ jY_0 & V_1 & -VX & 0 & 0 & \cdots & & & \\ 0 & -W_1X_1 & -W_1 & W_2 & W_2X_2 & 0 & 0 & \cdots & \\ 0 & -V_1X_1 & V_1 & V_2 & -V_2X_2 & 0 & 0 & \cdots & \\ & 0 & 0 & \ddots & & \ddots & & & \vdots \\ & & 0 & 0 & & & & & \\ & & & \cdots & & -W_{L-1}X_{L-1} & -W_{L-1} & I & \\ & & & & & -V_{L-1}X_{L-1} & V_{L-1} & jY_L \end{bmatrix} \begin{bmatrix} R \\ c1_1 \\ c2_1 \\ \vdots \\ \vdots \\ c1_{L-1} \\ c2_{L-1} \\ T \end{bmatrix} = \begin{bmatrix} \delta_{i0} \\ j\delta_{i0}n_0\cos(\theta) \\ 0 \\ \vdots \\ \vdots \\ \vdots \\ 0 \end{bmatrix},$$

and this boundary-matched system matrix equation may be solved to provide the reflectivity $R_i$ for each harmonic order i. For TE-polarized incident electromagnetic radiation 910, equations (1.6.1), (1.6.2), and (1.6.3) may be solved via a similar system matrix equation.

4. Transfer Matrix Formulation of the System Equation

As taught by "Stable Implementation of the Rigorous Coupled-Wave Analysis for Surface-Relief Dielectric Gratings: Enhanced Transmittance Matrix Approach", E. B. Grann and D. A. Pommet, *J. Opt. Soc. Am. A*, vol. 12, 1077–1086, May 1995, equation (1.4.2) may be written as $$\begin{bmatrix} c1_{l-1} \\ c2_{l-1} \end{bmatrix} = \begin{bmatrix} W_{l-1}X_{l-1} & W_{l-1} \\ V_{l-1}X_{l-1} & -V_{l-1} \end{bmatrix}^{-1} \begin{bmatrix} W_l & W_lX_l \\ V_l & -V_lX_l \end{bmatrix} \begin{bmatrix} c1_l \\ c2_l \end{bmatrix}, \quad (2.1.1)$$

and, for TM-polarized incident electromagnetic radiation 910, the reflectivity R may be coupled to the transmission T by repeated substitution of equation (2.1.1) for values of l from 1 to (L−1) into equations (1.4.1) and (1.4.3) to provide (1160) system matrix equation $$\begin{bmatrix} \delta_{i0} \\ jn_0\cos(\theta)\delta_{i0} \end{bmatrix} + \begin{bmatrix} I \\ -jY_0 \end{bmatrix} R = \qquad (2.1.2)$$

$$\prod_{l=1}^{L-1} \left\{ \begin{bmatrix} W_l & W_lX_l \\ V_l & -V_lX_l \end{bmatrix} \begin{bmatrix} W_lX_l & W_l \\ V_lX_l & -V_l \end{bmatrix}^{-1} \right\} \begin{bmatrix} I \\ jY_L \end{bmatrix} T,$$

where the pairs of matrices in curly brackets are arranged in ascending order in the layer variable l from left to right. Equation (2.1.2) may be solved to provide the reflectivity R. Similarly, for TE-polarized incident electromagnetic radiation 910 the reflectivity R may be coupled to the transmission T to provide (1160) system matrix equation $$\begin{bmatrix} \delta_{i0} \\ j\cos(\theta)\delta_{i0}/n_0 \end{bmatrix} + \begin{bmatrix} I \\ -jZ_0 \end{bmatrix} R = \qquad (2.1.3)$$

$$\prod_{l=1}^{L-1} \left\{ \begin{bmatrix} W_l & W_lX_l \\ V_l & -V_lX_l \end{bmatrix} \begin{bmatrix} W_lX_l & W_l \\ V_lX_l & -V_l \end{bmatrix}^{-1} \right\} \begin{bmatrix} I \\ jZ_L \end{bmatrix} T,$$

which may be solved for the reflectivity R.

According to the present specification, the matrix $$[T_l] \equiv \begin{bmatrix} W_l & W_lX_l \\ V_l & -V_lX_l \end{bmatrix} \begin{bmatrix} W_lX_l & W_l \\ V_lX_l & -V_l \end{bmatrix}^{-1} \qquad (2.1.4)$$

is termed the "transfer matrix" for the $l^{th}$ layer, and equations (2.1.2) and (2.1.3) may be written as $$\begin{bmatrix} \delta_{i0} \\ jn_0\cos(\theta)\delta_{i0} \end{bmatrix} + \begin{bmatrix} I \\ -jY_0 \end{bmatrix} R = [\Gamma_1][\Gamma_2][\Gamma_3]\cdots[\Gamma_{L-2}][\Gamma_{L-1}] \begin{bmatrix} I \\ jY_L \end{bmatrix} T, \qquad (2.1.5)$$

and $$\begin{bmatrix} \delta_{i0} \\ j\cos(\theta)\delta_{i0}/n_0 \end{bmatrix} + \qquad (2.1.6)$$

$$\begin{bmatrix} I \\ -jZ_0 \end{bmatrix} R =$$

$$[\Gamma_1][\Gamma_2][\Gamma_3]\cdots[\Gamma_{L-2}][\Gamma_{L-1}] \begin{bmatrix} I \\ jZ_L \end{bmatrix} T,$$

respectively. The transfer matrix $[\Gamma_l]$ is termed the 'transmittance' matrix in some references, such as the above-cited reference by E. B. Grann and D. A. Pommet. Note that in the present exemplary embodiment just as the wave-vector matrix $[A_l]$, and its eigenvector matrix $[W_l]$ and root-eigenvalue matrix $[Q_l]$ are only dependent on intra-layer parameters for the $l^{th}$ layer (and incident-radiation parameters), and the layer-transfer matrix $\Gamma_l$ is also only dependent on intra-layer parameters for the lth layer (and incident-radiation parameters). However, in contrast with the wave-vector matrix $[A_l]$, and its eigenvector matrix $[W_l]$ and root-eigenvalue matrix $[Q_l]$, the layer-translation matrix $[X_l]$ which appears in the layer-transfer matrix $[\Gamma_l]$ is dependent on the thickness $t_l$ of the $l^{th}$ layer. Although thickness t is an intra-layer parameter, for reasons that will become apparent below, thickness t will be classified as an aggregate-layer parameter in the present specification.

In the present exemplary embodiment, the "aggregate-layer transfer matrix" for layers li to lj can be defined as:

$$[T_{li \to lj}] \equiv \prod_{l=li}^{lj} \left( \begin{bmatrix} W_l & W_lX_l \\ V_l & -V_lX_l \end{bmatrix} \begin{bmatrix} W_lX_l & W_l \\ V_lX_l & -V_l \end{bmatrix}^{-1} \right), \qquad (2.1.7)$$

where the pairs of matrices on the right side of equation (2.1.7) are arranged in ascending order in the layer variable l from left to right. For example, $$[T_{3\to 4}] = \qquad (2.1.8)$$

$$\begin{bmatrix} W_3 & W_3X_3 \\ V_3 & -V_3X_3 \end{bmatrix} \begin{bmatrix} W_3X_3 & W_3 \\ V_3X_3 & -V_3 \end{bmatrix}^{-1} \begin{bmatrix} W_4 & W_4X_4 \\ V_4 & -V_4X_4 \end{bmatrix} \begin{bmatrix} W_4X_4 & W_4 \\ V_4X_4 & -V_4 \end{bmatrix}^{-1}.$$

Note that the aggregate-layer transfer matrix $[\Gamma_{li\to lj}]$ is only dependent on the characteristics of the $li^{th}$ through $lj^{th}$ layers (and the incident-radiation parameters). In terms of the aggregate-layer transfer matrices $[\Gamma_{li\to lj}]$, the system matrix equations for a profile which is discretized into n+1 aggregate-layer trapezoids are $$\begin{bmatrix} \delta_{i0} \\ jn_0\cos(\theta)\delta_{i0} \end{bmatrix} + \begin{bmatrix} I \\ -jY_0 \end{bmatrix} R = \qquad (2.1.9)$$

$$[\Gamma_{1\to l1}][\Gamma_{l1+1\to l2}][\Gamma_{l2+1\to l3}]\cdots[\Gamma_{ln+1\to L-1}]\begin{bmatrix} I \\ jY_L \end{bmatrix} T,$$

and $$\begin{bmatrix} \delta_{i0} \\ j\cos(\theta)\delta_{i0}/n_0 \end{bmatrix} + \begin{bmatrix} I \\ -jZ_0 \end{bmatrix} R = \qquad (2.1.10)$$

$$[\Gamma_{1\to l1}][\Gamma_{l1+1\to l2}][\Gamma_{l2+1\to l3}]\cdots[\Gamma_{ln+1\to L-1}]\begin{bmatrix} I \\ jZ_L \end{bmatrix} T,$$

for TM- and TE-polarizations, respectively. As described in detail below, caching and retrieval of aggregate-layer transfer matrices $[\Gamma_{li\to lj}]$ can be used to reduce the computation time required for generating spectra using rigorous coupled-wave analyses.

5. Caching and Retrieval of Aggregate-Layer Transfer Matrices

As presented above, the calculation of the diffraction of incident TE-polarized or TM-polarized radiation 910 from a periodic grating involves the generation of a system matrix equation (2.1.5) or (2.1.6), respectively, and its solution. The most computationally expensive portion of the RCWA computations flowcharted in FIGS. 11 and 12 can be the solution (1147) and (1247) for the eigenvectors $w_{l,i}$ and eigenvalues $\tau_{l,i}$ of wave-vector matrix $[A_l]$ of equation (1.3.7). The accuracy of the calculation of the eigenvectors $w_{l,i}$ and eigenvalues $\tau_{l,i}$ is dependent on the number of orders o utilized. As the number of orders o is increased, the computation time for solving the eigensystem increases exponentially with o. When performed in a typical computing environment with o=9 harmonic orders, the calculation of the eigenvectors and eigenvalues can take more than 85% of the total computation time.

In the present exemplary embodiment, a computer system 1500 can be used to perform the various calculations and operations described above. As depicted in FIG. 15, computer system 1500 can include an information input/output (I/O) equipment 1505, which is interfaced to a computer 1510 which includes a central processing unit (CPU) 1515 and a memory 1520. Although the CPU 1515 is depicted in FIG. 15 as a single unit, the CPU 1515 can include a number of processors configured to process in parallel. In order of increasing preference, the CPU 1515 includes four, eight, sixteen, thirty-two, or more high-speed parallel processors. The parallel processing capabilities of the CPU 1515 of the preferred embodiment allows for a substantial speed-up in the calculation of aggregate-layer transfer matrices $[\Gamma_{li\to lj}]$.

For instance, each parallel processor can be assigned to generate aggregate-layer transfer matrices $[\Gamma_{li\to lj}]$ over a separate range of wavelengths $\lambda$ since calculations at one wavelength $\lambda$ are independent of calculations at other wavelengths $\lambda$. The I/O equipment 1505 can also include a keyboard 1502 and mouse 1504 for the input of information, and a display 1501 and printer 1503 for the output of information. Many variations of this simple computer system 1500 can include systems with multiple I/O devices, multiple computers connected by Internet linkages, multiple computers connected by local area networks, devices that incorporate CPU 1515, memory 1520, and I/O equipment 1505 into a single unit, etc.

As will be described below, in the present exemplary embodiment, portions of the above-described analysis are pre-computed and cached, thereby reducing the computation time required to calculate the diffracted reflectivity produced by a periodic grating. Briefly, the pre-computation and caching can include:

pre-computation and caching (i.e., storage in a look-up table) of the permittivity $\epsilon(x)$, the harmonic components $\epsilon_i$ of the permittivity $\epsilon(x)$ and the permittivity harmonics matrix [E], and/or the permittivity $\epsilon(x)$, the inverse-permittivity harmonics $\pi_i$ and the inverse-permittivity harmonics matrix [P], for intra-layer parameters spanning an intra-layer parameters region $\{\mu\}$;

pre-computation and caching of the wave-vector matrix [A] for intra-layer parameters spanning an intra-layer parameters region $\{\mu\}$ and incident-radiation parameters spanning an incident-radiation parameters region $\{\kappa\}$;

pre-computation and caching of eigenvectors $w_{i,m}$ and eigenvalues $\tau_m$ of the wave-vector matrix [A] to form an eigenvector matrix [W], a root-eigenvalue matrix [Q], and a compound matrix [V] for intra-layer parameters spanning an intra-layer parameters region $\{\mu\}$ and incident-radiation parameters spanning an incident-radiation parameters region $\{\kappa\}$; and pre-computation and caching of aggregate-layer transfer matrices $[\Gamma_{li\to lj}]$ for aggregate-layer parameters spanning an aggregate-layer parameters region $\{\phi\}$.

Briefly, in the present exemplary embodiment, the use of the pre-computed and cached aggregate-layer transfer matrices $[\Gamma_{li\to lj}]$ to calculate the diffraction spectrum from a periodic grating can include:

construction of matrix equation (2.1.9) or (2.1.10) by retrieval of cached aggregate-layer transfer matrices $[\Gamma_{li\to lj}]$ corresponding to the aggregate-layer trapezoids 1030 of the grating 145 under consideration; and solution of the matrix equation (2.1.9) or (2.1.10) to determine the diffracted reflectivity $R_i$ for each harmonic order i.

Figure 16A:
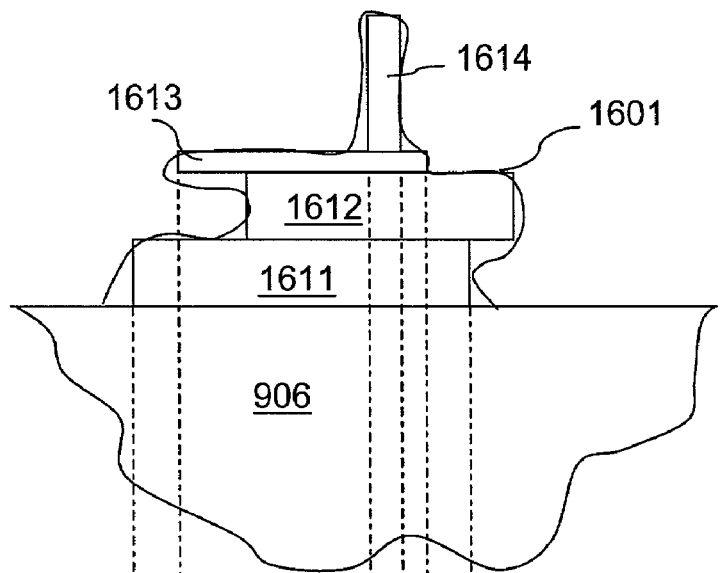
FIGS. 16A–16D depict exemplary ridge profiles.
Figure 16B:
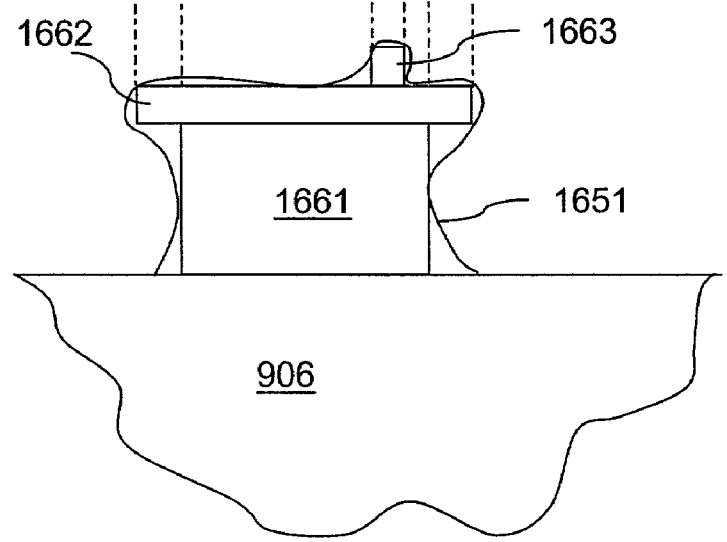

The intra-layer precalculation and caching portion is illustrated by consideration of the exemplary ridge profiles 1601 and 1651 shown in cross-section in FIGS. 16A and 16B, respectively. The profile 1601 of FIG. 16A is approximated by four slabs 1611, 1612, 1613 and 1614 of rectangular cross-section. Similarly, the profile 1651 of FIG. 16B is approximated by three slabs 1661, 1662, and 1663 of rectangular cross-section. The two exemplary ridge profiles 1601 and 1651 are each part of an exemplary periodic grating (other ridges not shown) which have the same grating period D, angle $\theta$ of incidence of the radiation 910, incident radiation wavelength $\lambda$, and the index of refraction $n_0$ of the atmospheric material between the ridges 1601 and 1651 is the same. It should be noted that slabs 1614 and 1663 do not have the same thicknesses t, nor do slabs 1613 and 1661, or slabs 1611 and 1662 have the same thicknesses t. However, slabs 1613 and 1661 have the same ridge slab width d, x-offset β, and index of refraction $n_r$. Similarly, slabs 1611 and 1662 have the same ridge slab width d, x-offset β, and index of refraction $n_r$, and slabs 1614 and 1663 have the same ridge slab width d, x-offset β, and index of refraction $n_r$. Note that the ridges can be mounted directly on a substrate, or on films deposited on a substrate, since a film can be considered to be a ridge having a width d equal to the pitch D.

Note that thickness t is not a parameter upon which the wave-vector matrix [A] is dependent. Although thickness t is actually an intra-layer parameter, for reasons that will become clear below, thickness t will be considered an aggregate-layer parameter. Therefore, the wave-vector matrices [A] are the same for slabs 1611 and 1662, 1613 and 1661, and 1614 and 1663, and the eigenvector matrices [W], the root-eigenvalue matrices [Q], and the compound eigensystem matrices [V] for slabs 1661, 1662 and 1663 are the same as the eigenvector matrices [W], the root-eigenvalue matrices [Q], and the compound eigensystem matrices [V] for slabs 1613, 1611 and 1614, respectively. Therefore, caching and retrieval of the eigensystem matrices [W], [Q], and [V] for slabs 1613, 1611 and 1614 prevents the need for recalculation of eigensystem matrices [W], [Q], and [V] for slabs 1661, 1662 and 1663, and can reduce the computation time. Additionally, the pre-calculation and caching of eigensystem matrices [W], [Q], and [V] for useful ranges and samplings of intra-layer parameters and incident-radiation parameters can reduce the computation time.

Figure 13:
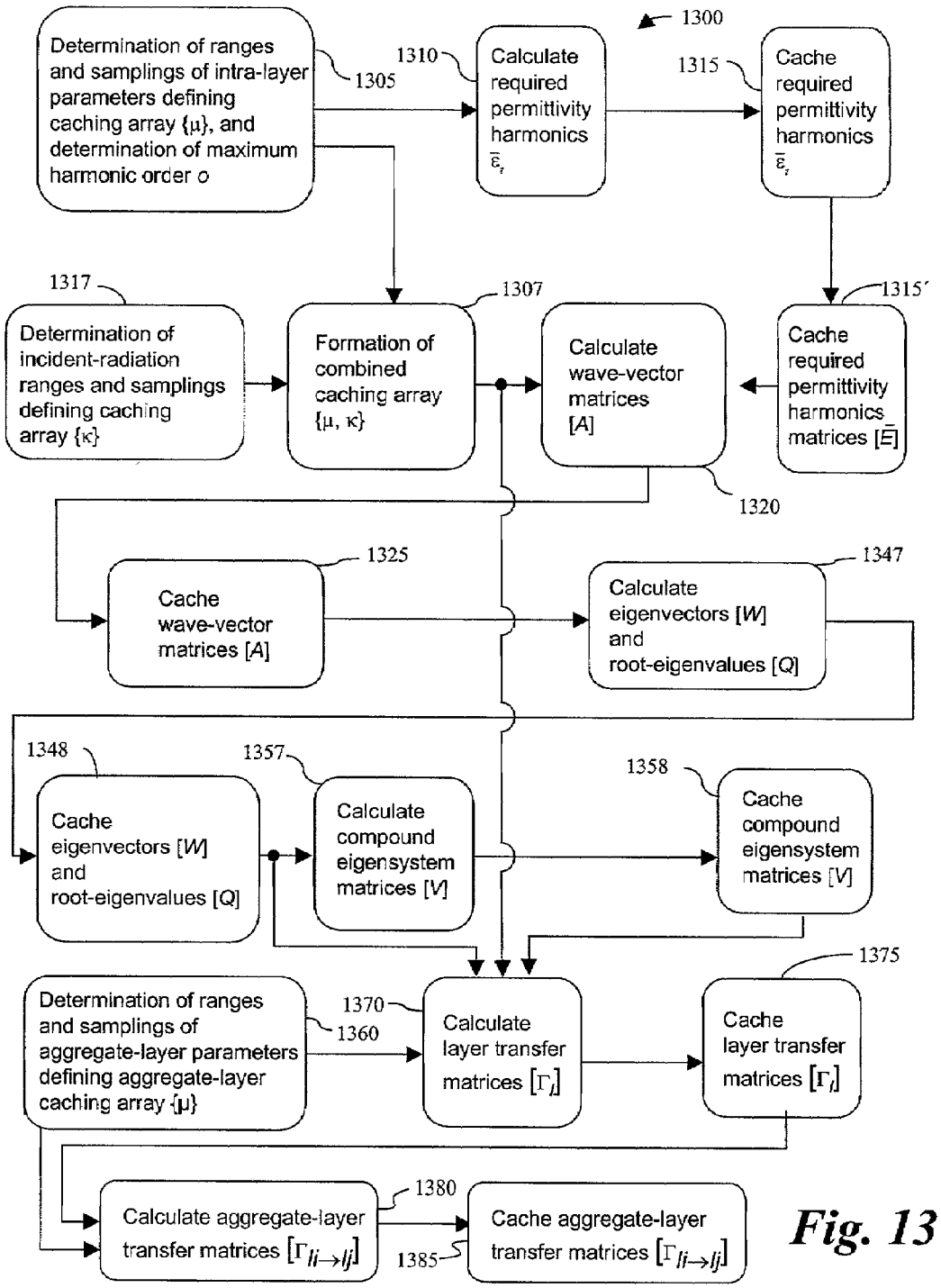
FIG. 13 depicts an exemplary process of generating simulated-diffraction signals.

As can be seen from equations (1.1.2), (1.1.3), (2.1.2) and (2.1.3), the permittivity harmonics $\epsilon_{l,i}$ and the inverse permittivity harmonics $\pi_{l,i}$ are only dependent on the following intra-layer parameters: the index of refraction of the ridges $n_r$, the index of refraction of the atmospheric material $n_0$, the pitch D, the ridge slab width d, and the x-offset β. As shown in the flowchart of FIG. 13, method (1300) begins with the determination (1305) of the ranges $n_{r,min}$ to $n_{r,max}$, $n_{0,min}$ to $n_{0,max}$, $D_{min}$ to $D_{max}$, $d_{min}$ to $d_{max}$, and $\beta_{min}$ to $\beta_{max}$, and sampling increments $\delta n_r$, $\delta n_0$, $\delta D$, $\delta d$, and $\delta\beta$ for the intra-layer parameters, i.e., the index of refraction of the ridges $n_r$, the index of refraction of the atmospheric material $n_0$, the pitch D, the ridge slab width d, and the x-offset β. The determination (1305) of the maximum harmonic order o must also be made. This information is forwarded from the I/O device 1505 to the CPU 1515. Typically, when applied to periodic gratings produced by semiconductor fabrication techniques, the ranges $n_{r,min}$ to $n_{r,max}$, $n_{0,min}$ to $n_{0,max}$, $D_{min}$ to $D_{max}$, $d_{min}$ to $d_{max}$, and $\beta_{min}$ to $\beta_{max}$ are determined based on knowledge and expectations regarding the fabrication materials, the fabrication process parameters, and other measurements taken of the periodic grating 145 or related structures. Similarly, when matching a measured diffraction spectrum to a library of calculated diffraction spectra to determine the dimensions of the periodic grating that created the measured diffraction spectrum, the sampling increments $\delta n_r$, $\delta n_0$, $\delta D$, $\delta d$, and $\delta\beta$, and maximum harmonic order o of the library, are chosen based on the resolution to which the intra-layer parameters $n_r$, $n_0$, D, d and β are to be determined. The intra-layer parameter ranges $n_{r,min}$ to $n_{r,max}$, $n_{0,min}$ to $n_{0,max}$, $D_{min}$ to $D_{max}$, $d_{min}$ to $d_{max}$, and $\beta_{min}$ to $\beta_{max}$, and increments $\delta n_r$, $\delta n_0$, $\delta D$, $\delta d$, and $\delta\beta$ define a five-dimensional intra-layer caching array $\{\mu\}$. More specifically, the caching array $\{\mu\}$ consists of intra-layer points with the $n_r$ coordinates being $\{n_{r,min}, n_{r,min}+\delta n_r, n_{r,min}+2\delta n_r, \ldots, n_{r,max}-2\delta n_r, n_{r,max}-\delta n_r, n_{r,max}\}$, the $n_0$ coordinates being $\{n_{0,min}, n_{0,min}+\delta n_0, n_{0,min}+2\delta n_0, \ldots,$ $n_{0,max}-2\delta n_0, n_{0,max}-\delta n_0, n_{0,max}\}$, the $n_0$ coordinates being $\{D_{min}, D_{min}+\delta D, D_{min}+2\delta D, \ldots, D_{max}-2\delta D, D_{max}-\delta D, D_{max}\}$, the d coordinates being $\{d_{min}, d_{min}+\delta d, d_{min}+2\delta d, \ldots, d_{max}-2\delta d, d_{max}-\delta d, d_{max}\}$, and the β coordinates being $\{\beta_{min}, \beta_{min}+\delta\beta, \beta_{min}+2\delta\beta, \ldots, \beta_{max}-2\delta\beta, \beta_{max}-\delta\beta, \beta_{max}\}$. In other words, the intra-layer caching array $\{\mu\}$ is defined as a union of five-dimensional coordinates as follows:

$$\{\mu\} = \bigcup_{i,j,k,l,m} (n_{r,\min}+i\delta n_r, n_{0,\min}+j\delta n_0, D_{\min}+ \quad (3.1.1)$$

$$k\delta D, d_{\min}+m\delta d, \beta_{\min}+n\delta\beta),$$

where i, j, k, m and n are integers with value ranges of $$0 \leq i \leq (n_{r,max}-n_{r,min})/\delta n_r, \quad (3.1.2a)$$

$$0 \leq j \leq (n_{0,max}-n_{0,min})/\delta n_0, \quad (3.1.2b)$$

$$0 \leq k \leq (D_{max}-D_{min})/\delta D, \quad (3.1.2c)$$

$$0 \leq m \leq (d_{max}-d_{min})/\delta d, \quad (3.1.2d)$$

and $$0 \leq n \leq (\beta_{max}-\beta_{min})/\delta\beta. \quad (3.1.2.e)$$

It should be noted that the layer subscript, l, is not used in describing the intra-layer parameters $n_r$, $n_0$, D, d, and β used in the layer-property caching array $\{\mu\}$ because each particular point in the layer-property caching array $\{\mu\}$ may correspond to none, one, more than one, or even all of the layers 1025 of a particular periodic grating 145.

As shown in FIG. 13, for each point in the layer-property caching array $\{\mu\}$ the "formulation-required" permittivity harmonics $\bar{\epsilon}_i$ are calculated (1310) by the CPU 1515 and cached (1315) in memory 1520, and the "formulation-required" permittivity harmonics matrices [E] are compiled from the cached formulation-required permittivity harmonics $\bar{\epsilon}_i$ i and cached (1315') in memory 1520. For RCWA analyses of TE-polarized incident radiation 910, or RCWA analyses of TM-polarized incident radiation 910 according to the formulation of equations (1.5.3) and (1.5.11), the formulation-required permittivity harmonics $\bar{\epsilon}_i$ are the permittivity harmonics si calculated (1310) according to equations (1.1.2) and (1.1.3), and the formulation-required permittivity harmonics matrix [E] is the permittivity harmonics matrix [E] formed as per equation (1.1.4).

Similarly, for RCWA analyses of TM-polarized incident radiation 910 according to the formulation of equations (1.5.1) and (1.5.9) or equations (1.5.2) and (1.5.10), the formulation-required permittivity harmonics $\bar{\epsilon}_i$ are the permittivity harmonics $\epsilon_l$ calculated (1310) according to equations (1.1.2) and (1.1.3) and the inverse-permittivity harmonics $\pi_i$ calculated (1310) according to equations (1.5.6) and (1.5.7), and the formulation-required permittivity harmonics matrices [E] are the permittivity harmonics matrix [E] formed from the permittivity harmonics $\epsilon_i$ as per equation (1.1.4) and the inverse-permittivity harmonics matrix [P] formed from the inverse-permittivity harmonics $\pi_i$ as per equations (1.5.6) and (1.5.7).

As per equations (1.3.7), (1.5.1), (1.5.2) and (1.5.3), the wave-vector matrix [A] is dependent on the required permittivity harmonics matrices [E] and the matrix [$K_x$]. The matrix [$K_x$], in addition to being dependent on "global" layer-property parameters (i.e., the atmospheric index of refraction $n_0$ and pitch D), is dependent on incident-radiation parameters, i.e., the angle of incidence θ and the wavelength λ of the incident radiation 910. As shown in the flowchart of FIG. 13, ranges $\theta_{min}$ to $\theta_{max}$ and $\lambda_{min}$ to $\lambda_{max}$, and increments δθ and δλ are determined (1317) for the incidence angle θ and wavelength λ, and forwarded from the I/O device 1505 to the CPU 1515. The incident-radiation caching array {κ} is defined as a union of two-dimensional coordinates as follows:

$$\{\kappa\} = \underset{n,o}{U}(\theta_{min} + p\delta\theta, \lambda_{min} + q\delta\lambda) \quad (3.1.3)$$

where p and q are integers with value ranges of $$0 \leq p \leq (\theta_{max} - \theta_{min})/\delta\theta, \quad (3.1.4a)$$

$$0 \leq q \leq (\lambda_{max} - \lambda_{min})/\delta\lambda. \quad (3.1.4b)$$

The combined caching array {μ, κK} is formed (1307) by the union of coordinates as follows:

$$\{\mu, \kappa\} = \underset{i,j,k,l,m}{U}(n_{r,min} + i\delta n_r, n_{0,min} + j\delta n_0, D_{min} + k\delta D, d_{min} + \quad (3.1.5)$$

$$m\delta d, \beta_{min} + n\delta\beta, \theta_{min} + p\delta\theta, \lambda_{min} + q\delta\lambda)$$

where i, j, k, m, n, p and q satisfy equations (3.1.2a), (3.1.2b), (3.1.2c), (3.1.2d), (3.1.4a) and (3.1.4b). Typically, the ranges $\theta_{min}$ to $\theta_{max}$ and $\lambda_{min}$ to $\lambda_{max}$ are determined (1317) based on knowledge and expectations regarding the apparatus (not shown) for generation of the incident radiation 910 and the apparatus (not shown) for measurement of the diffracted radiation 914. Similarly, the sampling increments δθ and δλ are determined (1317) based on the resolution to which the layer-property parameters $n_r$, $n_0$, D, d, and β are to be determined, and/or the resolution to which the incident-radiation parameters θ and λ can be determined. For each point in the combined caching array {μ, κ}, the wave-vector matrix [A] is calculated (1320) by the CPU 1515 according to equation (1.3.7), (1.5.1), (1.5.2) or (1.5.3) and cached (1225).

Since the wave-matrix matrix [$A_l$] is only dependent on incident-radiation parameters (angle of incidence θ of the incident radiation 910, wavelength λ of the incident radiation 910) within layer l, and intra-layer parameters (index of refraction of the ridges $n_r$, index of refraction of the atmospheric material $n_0$, pitch D, ridge slab width d, x-offset β), and it follows that the eigenvector matrix [$W_l$] and the root-eigenvalue matrix [$Q_l$] are also only dependent on the incident-radiation parameters θ and λ, and the layer-property parameters $n_r$, $n_0$, D, d, and β within layer l. According to a preferred embodiment, the eigenvector matrix [$W_l$] and its root-eigenvalue matrix [$Q_l$] are calculated (1347) by the CPU 1515 and cached (1348) in memory 1520 for each point in the combined caching array {μ, κ}. The calculation (1347) of the eigenvector matrices [$W_l$] and the root-eigenvalue matrices [$Q_l$] can be performed by the CPU 1515 using a standard eigensystem solution method, such as singular value decomposition (see Chapter 2 of *Numerical Recipes*, W. H. Press, B. P. Glannery, S. A. Teukolsky and W. T. Vetterling, Cambridge University Press, 1986). The matrix [V], where [V]=[W][Q], is then calculated (1357) by the CPU 1515 and cached (1358) in memory 1520.

Then, a library of useful aggregates of layers is generated. It should be noted that although the use of aggregate-layer trapezoids has been described, useful aggregates of layers may have other shapes as well. For instance, useful aggregates of layers may have more than four corners, may have convex as well as concave corners, may have curved sides, etc. Generally, aggregate-layer trapezoids will have horizontal top and bottom edges, so that boundaries between aggregate-layer trapezoids will coincide with boundaries between harmonic expansion layers 1025.

Figure 17:
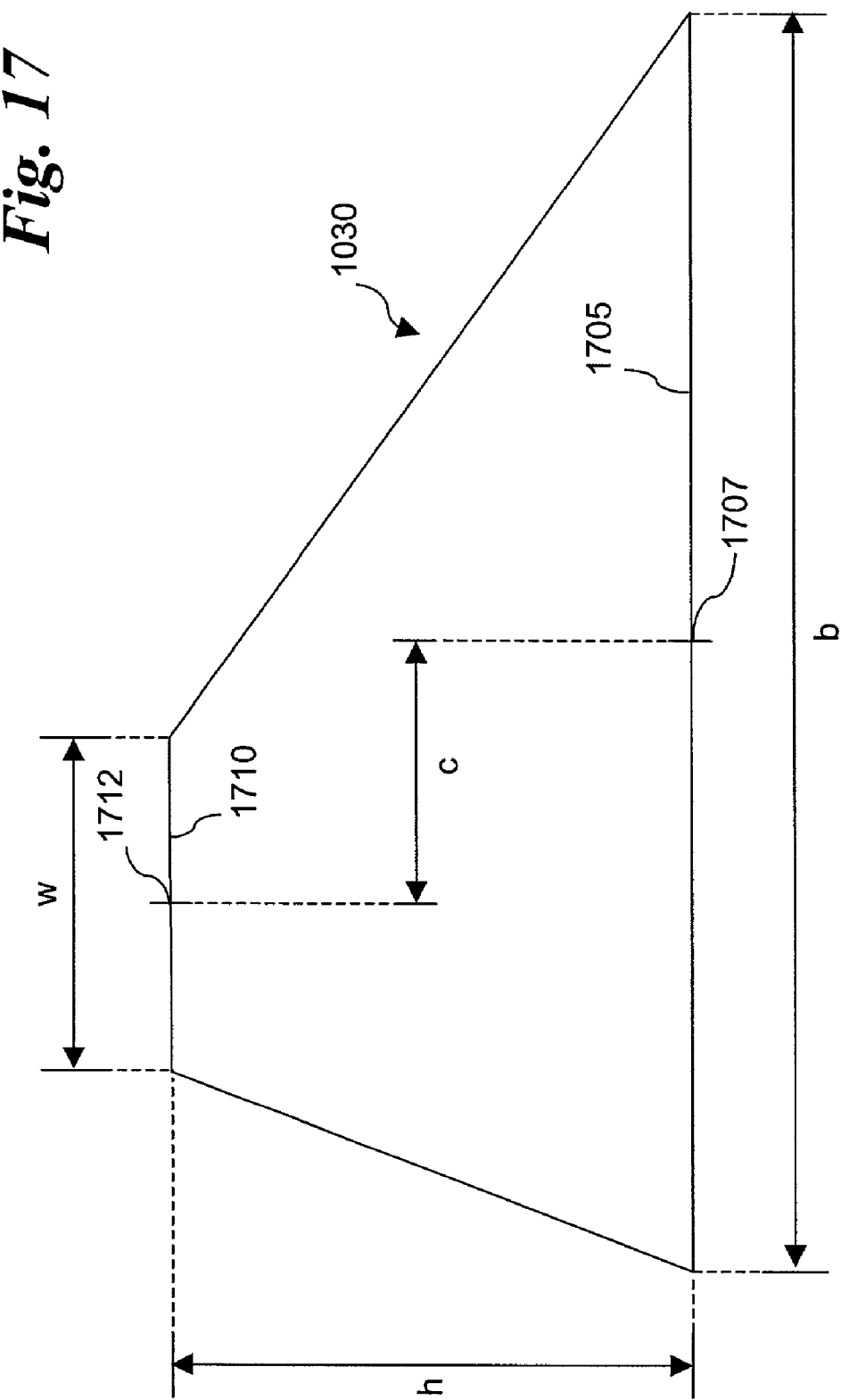
FIG. 17 depicts an exemplary aggregate-layer trapezoid.

As shown in FIG. 17, aggregate-layer trapezoids are described by four aggregate-layer parameters: the width b of the base 1705 of the trapezoid 1030, the width w of the top 1710 of the trapezoid 1030, the height h of the trapezoid 1030, and the distance offset c between the center 1707 of the base 1705 of the trapezoid 1030 and center 1712 of the top 1710 of the trapezoid 1030. Alternatively, the offset between the center 1707 of the base 1705 of the trapezoid 1030 and center 1712 of the top 1710 of the trapezoid 1030 may be given by a parameter which is an angle or a dimensionless ratio.

Figure 10C:
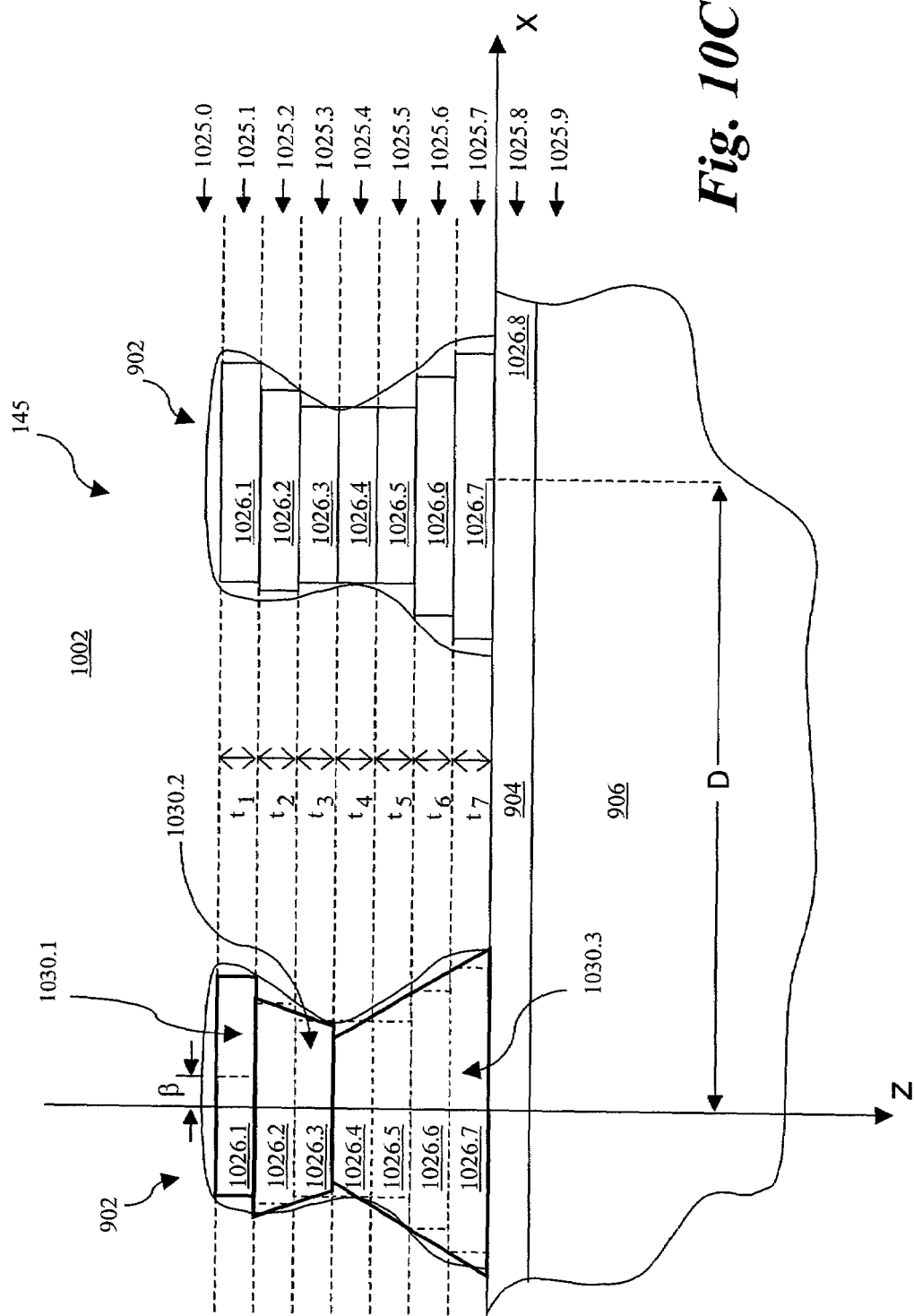
Figure 11:
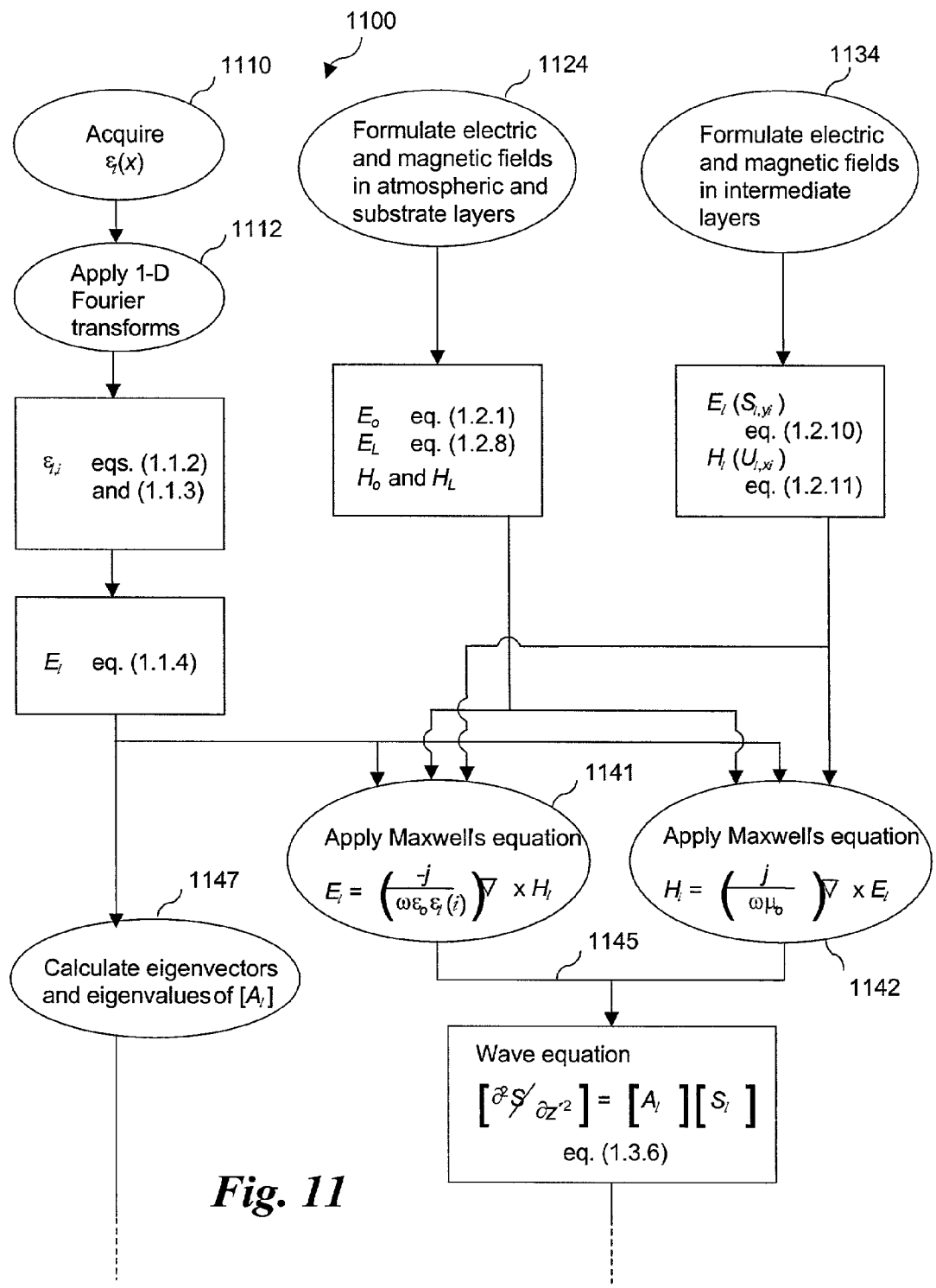
FIG. 11 depicts an exemplary coupled-wave analysis.
Figure 11:
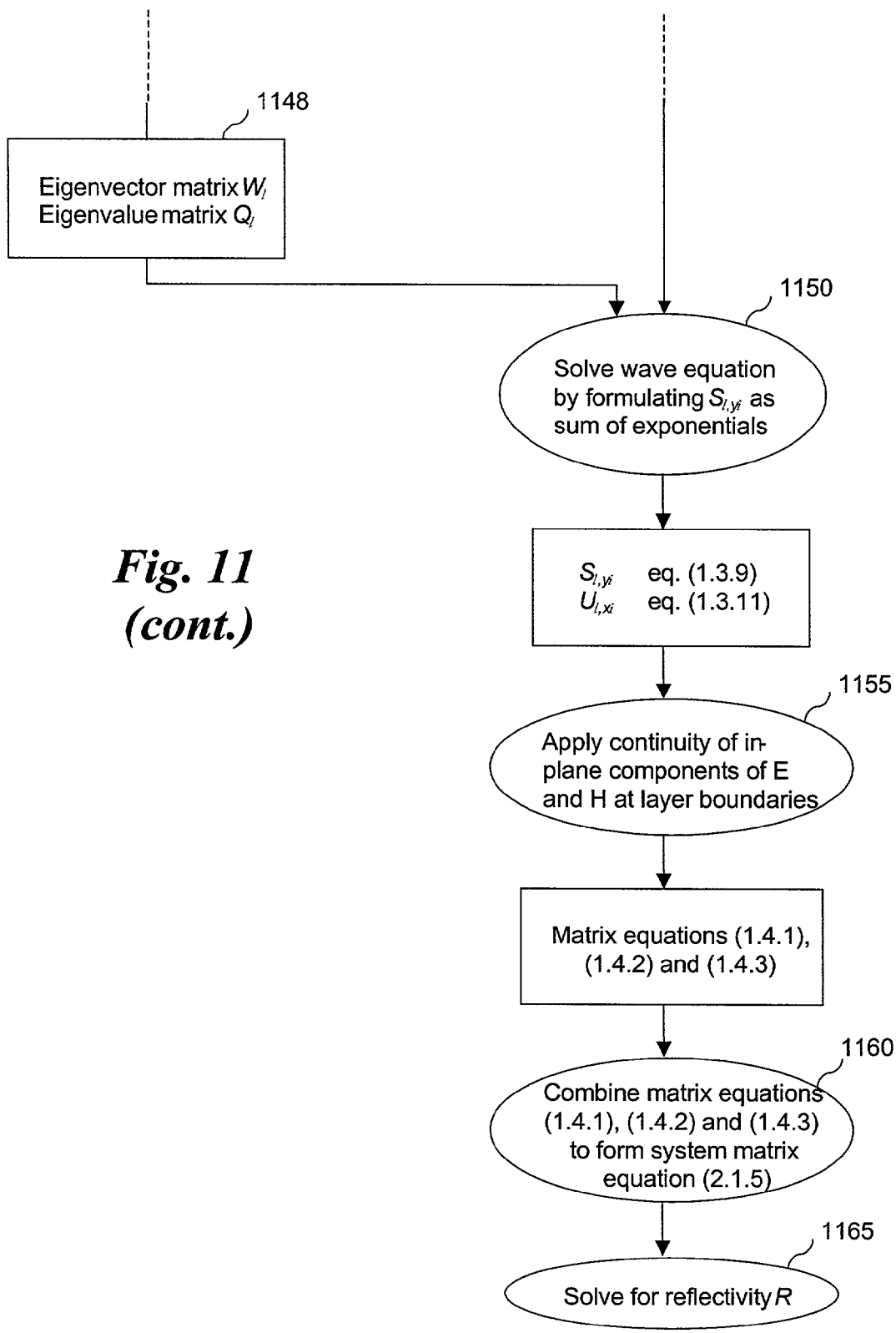

The left ridges of FIGS. 10B and 10C show groupings of the rectangular slabs 1026 into aggregate-layer trapezoids 1030 with side edges which approximately follow the side contours of the rectangular slabs 1026. In FIG. 10B, rectangular slabs 1026.1 and 1026.2 are grouped into the upper aggregate-layer trapezoid 1030.1, rectangular slabs 1026.3 and 1026.4 are grouped into the center aggregate-layer trapezoid 1030.2, which happens to be rectangular, and rectangular slabs 1026.5, 1026.6 and 1026.7 are grouped into the lower aggregate-layer trapezoid 1030.3. It should be noted that the upper and lower trapezoids 1030.1 and 1030.3 have side edges that are not vertical, while the rectangular slabs 1026 in each group represented by a trapezoid 1030.1 and 1030.3 have vertical side edges. The number of aggregate-layer trapezoids into which the rectangular slabs 1026 are grouped, and the particular assignment of rectangular slabs 1026 to aggregate-layer trapezoid 1030.3, will depend on the algorithm used to determine the groupings. For instance, in FIG. 10C, rectangular slab 1026.1 is represented by the upper, rectangular aggregate-layer trapezoid 1030.1, rectangular slabs 1026.2 and 1026.3 are grouped into the center aggregate-layer trapezoid 1030.2, and rectangular slabs 1026.4, 1026.5, 1026.6 and 1026.7 are grouped into the lower aggregate-layer trapezoid 1030.3. In a very crude approximation, rectangular slabs 1026.1 through 1026.7 could be represented by a single aggregate-layer trapezoid. Generally, the accuracy of a representation with aggregate-layer trapezoids will increase with the number of aggregate-layer trapezoids that are used, until the number of aggregate-layer trapezoids approaches the number (L−1) of rectangular slabs 1026 in a ridge 902. Typically, while between 16 and 25 rectangular slabs 1026 are required to accurately represent a profile, only 2 to 4 aggregate-layer trapezoids 1030 are required to accurately represent a profile. Therefore, even ignoring the speed-up due to caching, the calculation of the matrix product according to equations (2.1.9) or (2.1.10) for three aggregate-layer transfer matrices [$\Gamma_{li \to lj}$] can be seven times faster than the calculation of the matrix product according to equations (2.1.5) or (2.1.6) for 21 non-aggregate layer transfer matrices [$\Gamma_l$].

Figure 16C:
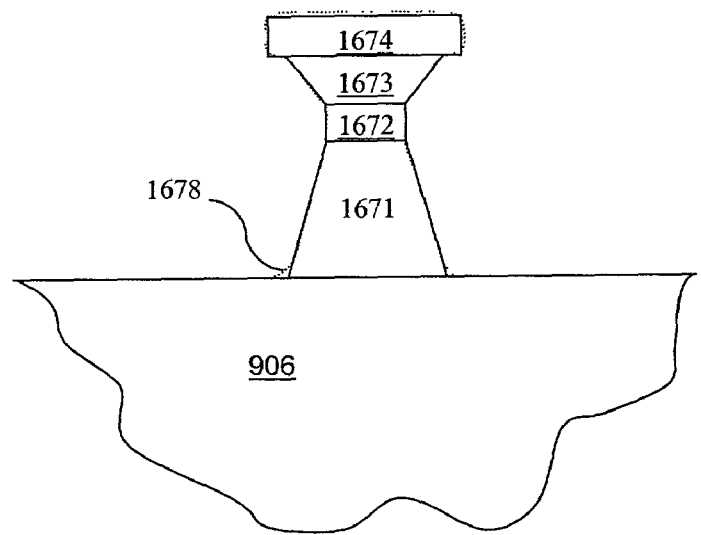
Figure 16D:
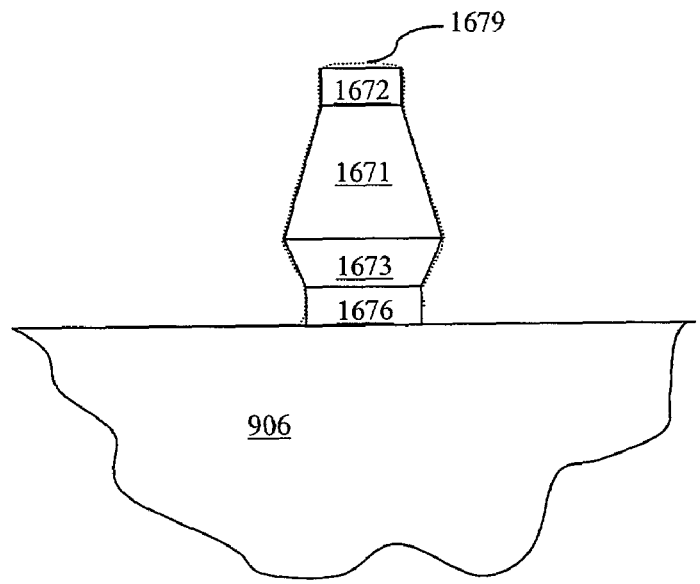

The aggregate-layer precalculation and caching portion is illustrated by consideration of the exemplary ridge profiles 1678 and 1679 shown in cross-section in FIGS. 16C and 16D, respectively. The profile 1678 of FIG. 16A is approximated by four aggregate-layer trapezoids 1671, 1672, 1673, and 1674. Similarly, the profile 1679 of FIG. 16D is approximated by four aggregate-layer trapezoids 1671, 1672, 1673, and 1676. The two exemplary ridge profiles 1678 and 1679 are each part of exemplary periodic gratings (other ridges not shown) which have the same grating period D, angle θ of incidence of the radiation, incident radiation wavelength λ, and index of refraction $n_0$ of the atmospheric material. The aggregate-layer trapezoid 1671 has the same base width b, top width w, height h and top-base offset c in both FIGS. 16C and 16D. Furthermore, although not discernible from FIGS. 16C and 16D, the index of refraction $n_r$ of aggregate-layer trapezoid 1671 is the same in both FIGS. 16C and 16D. Similarly, aggregate-layer trapezoids 1672 and 1673 have the same base width b, top width w, height h, top-base offset c, and index of refraction $n_r$ in both FIGS. 16C and 16D. However, aggregate-layer trapezoids 1674 and 1676 of FIGS. 16C and 16D have no equivalents in FIGS. 16D and 16C, respectively.

If aggregate-layer trapezoid 1671 in FIG. 16C and aggregate-layer trapezoid 1671 in FIG. 16D are composed of sets of rectangular slabs of the same dimensions (i.e., the same thicknesses t and widths d) which are stacked in the same order, then, as per equation (2.1.7), the aggregate-layer transfer matrix $[\Gamma_{li \to lj}]$ is the same for aggregate-layer trapezoid 1671 in FIG. 16C and aggregate-layer trapezoid 1671 in FIG. 16D. Similarly, if aggregate-layer trapezoids 1672 and 1673 in FIG. 16C and aggregate-layer trapezoids 1672 and 1673 in FIG. 16D are composed of sets of rectangular slabs of the same dimensions which are stacked in the same order, then the aggregate-layer transfer matrix $[\Gamma_{li \to lj}]$ is the same for the trapezoids 1672 and 1673 in FIG. 16C and the trapezoids 1672 and 1673 in FIG. 16D, respectively. Therefore, caching and retrieval of the aggregate-layer transfer matrices $[\Gamma_{li \to lj}]$ for aggregate-layer trapezoids 1671, 1672 and 1673 prevents the need for recalculation of the aggregate-layer transfer matrices $[\Gamma_{li \to lj}]$ and reduces the computation time. Additionally, the precalculation and caching of aggregate-layer transfer matrices $[\Gamma_{li \to lj}]$ for useful ranges and samplings of incident-radiation parameters, intra-layer parameters and aggregate-layer parameters can substantially reduce the computation time when multiple spectra utilizing those aggregate-layer transfer matrices $[\Gamma_{li \to lj}]$ are to be generated.

The mapping from rectangular slabs to aggregate-layer trapezoids 1030 is accomplished by a least-squares fit of the sides of the rectangular slabs to straight lines. Initially, the lengths of the fit lines are a substantial fraction of the total height of the profile. However, if the goodness-of-fit exceeds a critical value, the length of a fit line is reduced until the goodness-of-fit is below the critical value. It should be noted that the mapping from sets of stacked rectangular slabs to aggregate-layer transfer matrices $[\Gamma_{li \to lj}]$ is generally many-to-one. For instance, for the rectangular trapezoid 1672, the rectangular slabs that it represents might all have sides which are well-aligned with the sides of the rectangular trapezoid 1672. Or, the left and right sides of the rectangular slabs might deviate somewhat from the left and right sides of the rectangular trapezoid 1672, but have an average left-side position coincident with the left side of the trapezoid 1672 and an average right-side position coincident with the right side of the trapezoid 1672. Therefore, due to the many-to-one mapping, a retrieved aggregate-layer transfer matrix $[\Gamma_{li \to lj}]$ generally only provides an approximation to the aggregate-layer transfer matrix $[\Gamma_{li \to lj}]$ that would actually be generated by the set of rectangular slabs.

As shown in the flowchart of FIG. 13, the ranges $w_{min}$ to $w_{max}$, $b_{min}$ to $b_{max}$, $h_{min}$ to $h_{max}$, and $c_{min}$ to $c_{max}$, and sampling increments δw, δb, δh, and δc for the aggregate-layer parameters (i.e., the base width b, the top width w, the height h, and the base-top offset c) are determined (1360), and forwarded from the I/O device 1505 to the CPU 1515. Typically, when applied to periodic gratings produced by semiconductor fabrication techniques, the ranges $w_{min}$ to $w_{max}$, $b_{min}$ to $b_{max}$, $h_{min}$ to $h_{max}$, and $c_{min}$ to $c_{max}$ are determined based on knowledge and expectations regarding the fabrication materials, the fabrication process parameters, and other measurements taken of the periodic grating 145 or related structures. Similarly, when matching a measured diffraction spectrum to a library of calculated diffraction spectra to determine the dimensions of the periodic grating that created the measured diffraction spectrum, the sampling increments δw, δb, δh, and δc are chosen based on the resolution to which the aggregate-layer parameters w, b, h and c are to be determined. The aggregate-layer parameter ranges $w_{min}$ to $w_{max}$, $b_{min}$ to $b_{max}$, $h_{min}$ to $h_{max}$, and $c_{min}$ to $c_{max}$, and increments δw, δb, δh, and δc define a four-dimensional aggregate-layer caching array $\{\phi\}$. More specifically, the aggregate-layer caching array $\{\phi\}$ consists of aggregate-layer points with the w coordinates being $\{w_{min}, w_{min}+\delta w, w_{min}+2\delta w, \ldots, w_{max}-\delta w, w_{max}\}$, the b coordinates being $\{b_{min}, b_{min}+\delta b, b_{min}+2\delta b, \ldots, b_{max}-\delta b, b_{max}\}$, the h coordinates being $\{h_{min}, h_{min}+\delta h, h_{min}+2\delta h, \ldots, h_{max}-2\delta h, h_{max}-\delta h, h_{max}\}$, and the c coordinates being $\{c_{min}, c_{min}+\delta c, c_{min}+2\delta c, \ldots, c_{max}-2\delta c, c_{max}-\delta c, c_{max}\}$. In other words, the aggregate-layer caching array $\{\phi\}$ is defined as a union of four-dimensional coordinates as follows:

$$\{\phi\} = \bigcup_{i,j,k,m} (w_{\min} + i\delta w, b_{\min} + j\delta b, h_{\min} + k\delta h, c_{\min} + m\delta c), \quad (3.1.6)$$

where i, j, k and m are integers with value ranges of $$0 \leq i \leq (w_{max} - w_{in})/\delta w, \quad (3.1.7a)$$

$$0 \leq j \leq (b_{max} - b_{min})/\delta b, \quad (3.1.7b)$$

$$0 \leq k \leq (h_{max} - h_{min})/\delta h, \quad (3.1.7c)$$

and $$0 \leq m \leq (c_{max} - c_{min})/\delta c. \quad (3.1.7.d)$$

It should be noted that if any of the intra-layer parameters $n_r$, $n_0$, D, d, and β, any of the incident-radiation parameters θ and λ, or any of the aggregate-layer parameters b, w, h and c are known to sufficient accuracy, then a single value, rather than a range of values, of the parameter may be used, and the dimensionality of the corresponding caching array $\{\mu\}$, $\{\kappa\}$ or $\{\phi\}$ is effectively reduced. It should also be understood that the incident-radiation parameters region, the intra-layer parameters region and/or the aggregate-layer parameters region need not be hyper-rectangles, and the incident-radiation parameters region, the intra-layer parameters region and/or the aggregate-layer parameters region need not be sampled on a uniform grid. For instance, a sampling may be performed using a stochastic sampling method. Furthermore, the sampling density need not be uniform. For instance, the sampling density may decrease near the boundaries of a parameters region if circumstances near the boundaries are less likely to occur.

Once the range and sampling for the aggregate-layer caching array $\{\phi\}$ is determined (1360), layer transfer matrices $[\Gamma_l]$ are calculated (1370) by the CPU 1515 for each aggregate-layer trapezoid 1030, and cached (1375) in memory 1520 in the aggregate-layer caching array $\{\phi\}$. As shown in FIG. 13, the calculation of the layer transfer matrices [$\Gamma_l$] utilizes the cached eigenvectors [$W_l$], root-eigenvalues [$Q_l$], and compound eigensystem matrices [$V_l$]. Furthermore, due to the dependence of the layer transfer matrix [$\Gamma_l$] on the layer translation matrix [$X_l$], as per equation (2.1.4), the thickness t of the rectangular slab 1026 is provide for the calculation. As mentioned above, although thickness t is actually an intra-layer parameter, thickness t is considered an aggregate-layer parameter for the purposes of the present specification since it is not utilized until the calculation (1370) of the layer transfer matrices [$\Gamma_l$]. Utilizing the cached layer transfer matrices [$\Gamma_l$], aggregate-layer transfer matrices [$\Gamma_{li \to lj}$] are calculated (1370) by the CPU 1515 for each point in the aggregate-layer caching array $\{\varphi\}$, and cached (1385) in memory 1520.

Figure 14:
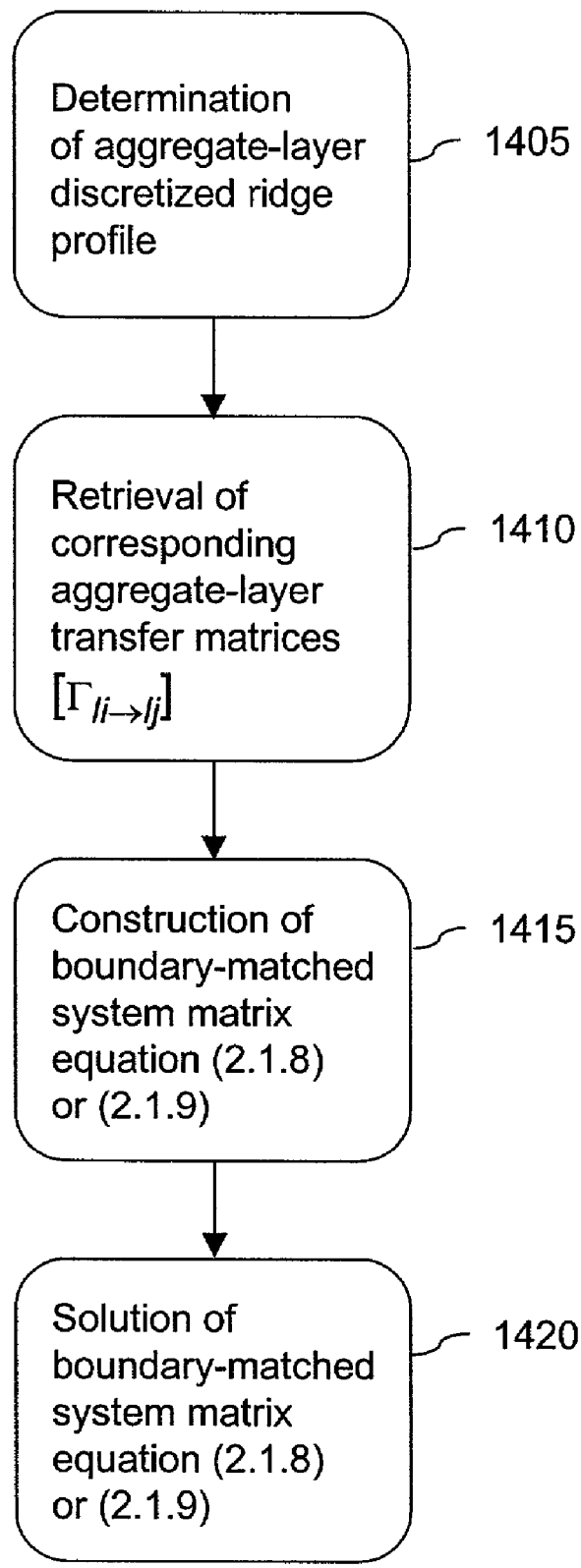
FIG. 14 depicts another exemplary process of generating simulated-diffraction signals.

The use of pre-computed and cached aggregate-layer transfer matrices [$\Gamma_{li \to lj}$] is shown in FIG. 14. Use of the cached aggregate-layer transfer matrices [$\Gamma_{li \to lj}$] begins by aggregate-layer discretizing a ridge profile and determining the parameters describing the aggregate-layer discretized ridge profile. In particular, the incident-radiation parameters (i.e., the angle of incidence $\theta$ and the wavelength $\lambda$ of the incident radiation), the intra-layer parameters (i.e., index of refraction of the ridges $n_r$, the index of refraction of the atmospheric material $n_0$, the pitch D, the ridge slab width d, and the x-offset $\beta$) for each rectangular slab 1026 in each aggregate-layer trapezoid 1030, and the aggregate-layer parameters (i.e., the base width b, the top width w, the height h, and the base-top distance offset c) for each aggregate-layer trapezoid 1030 are determined (1405) and forwarded via the I/O device 1505 to the CPU 1515.

Once the incident-radiation, intra-layer, and aggregate-layer parameters for an aggregate-layer discretized profile are determined (1405), the cached aggregate-layer transfer matrices [$\Gamma_{li \to lj}$] for the aggregate-layer trapezoids of the discretized ridge profile are retrieved (1410) from memory 1520 for use by the CPU 1515 in constructing (1415) the system matrix equation (2.1.9) or (2.1.10). The CPU 1515 then solves (1420) the boundary-matched system matrix equation (2.1.9) or (2.1.10) for the reflectivity $R_i$ of each harmonic order from $-o$ to $+o$ and each wavelength $\lambda$ of interest, and forwards the results to an output device 1505 such as the display 1501, printer 1503, or the like.

Figure 18:
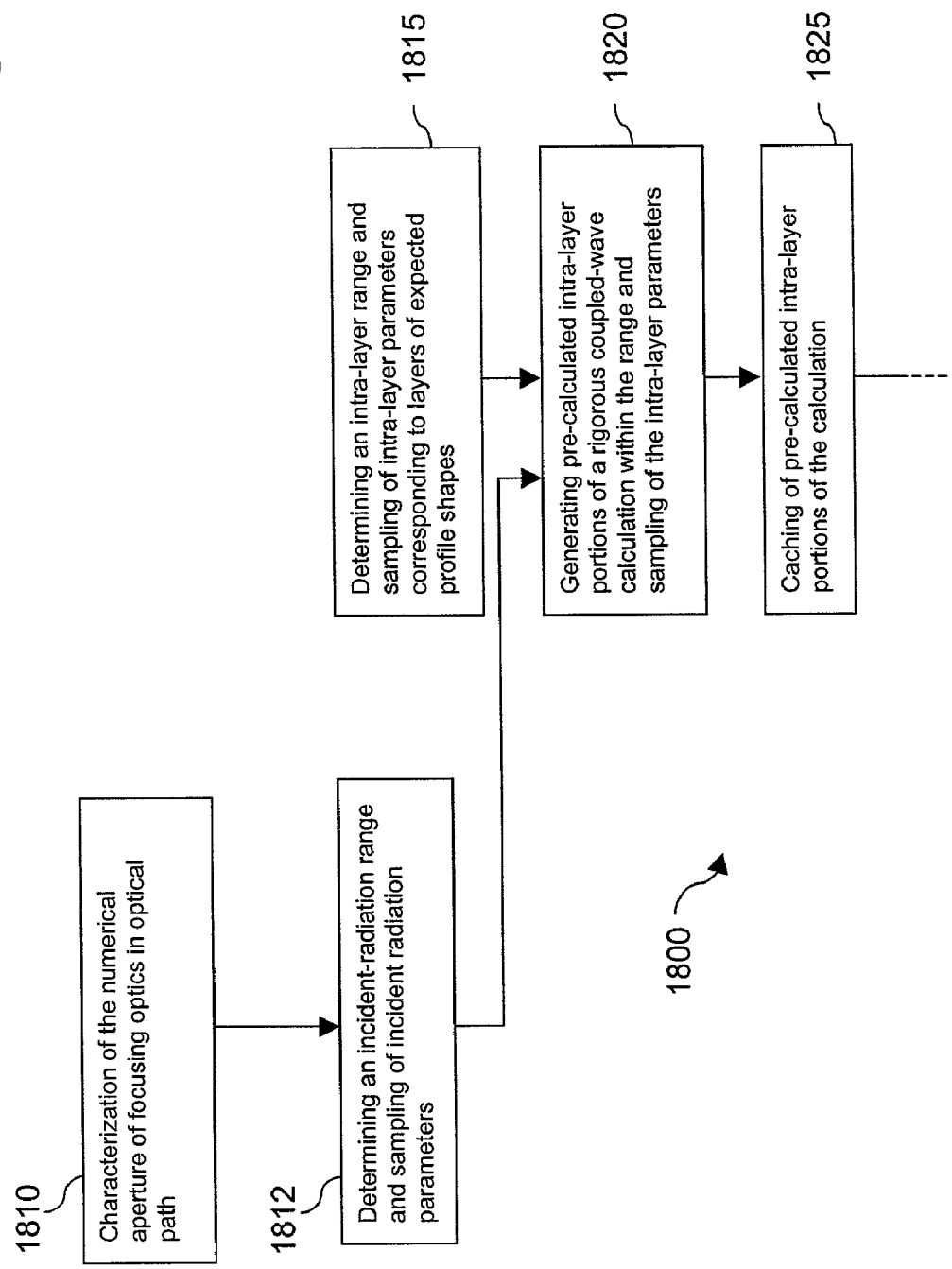
FIG. 18 depicts an exemplary process of generating a library of simulated-diffraction signals.
Figure 18:
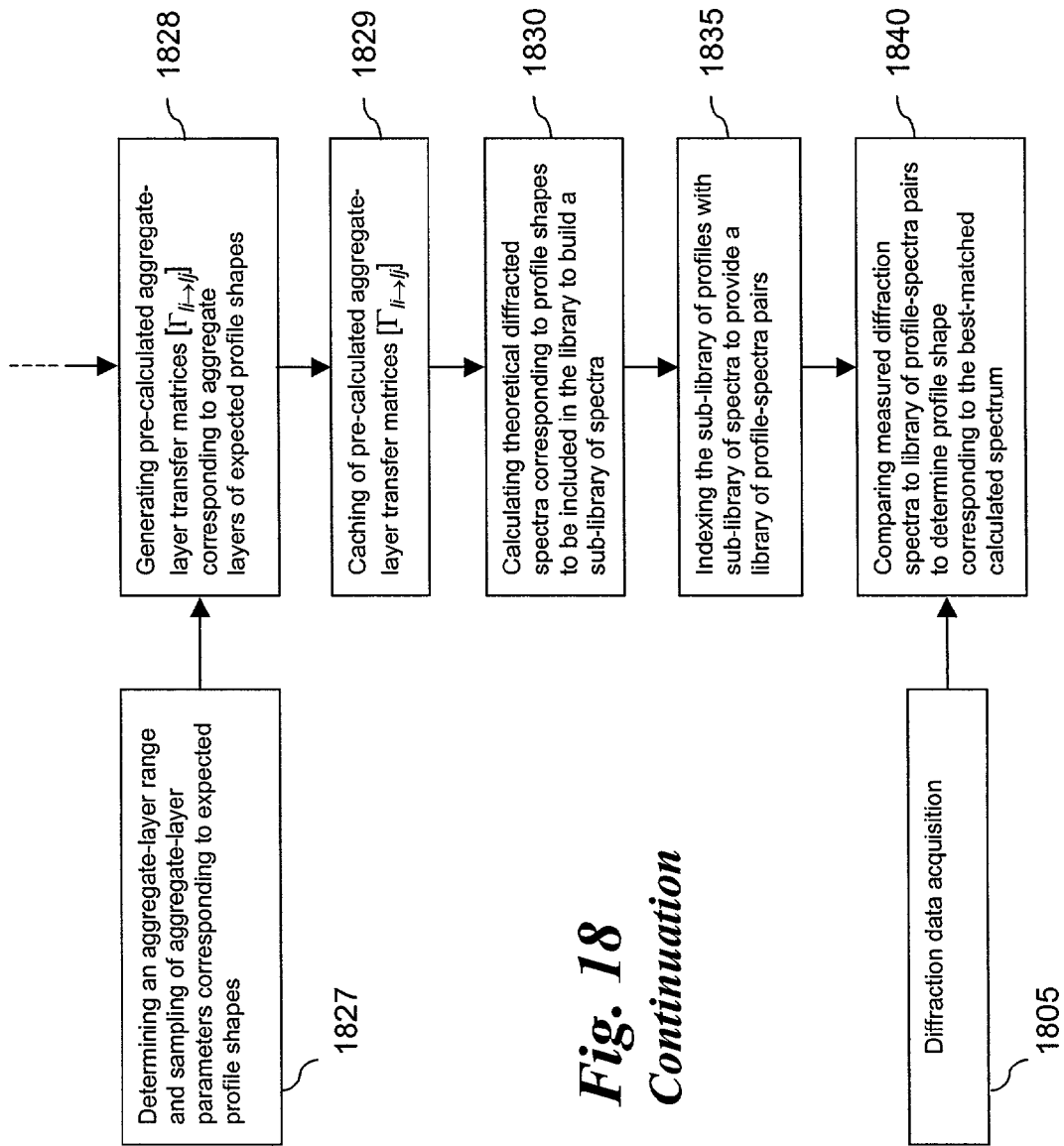

FIG. 18 presents a flowchart for the use of a library of profile-spectrum pairs, and use of the library to determine the profile corresponding to a measured spectrum. As shown in FIG. 18, the numerical aperture of the focusing optics in the optical path of the reflectometry or ellipsometry configuration is characterized (1810), and the range and sampling of incident-radiation parameters (i.e., incidence angle $\theta$ and wavelength $\lambda$) required for the calculation of the simulated diffraction spectra are determined (1812). Ranges and samplings of intra-layer parameters (i.e., the index of refraction of the ridges $n_r$, the index of refraction of the atmospheric material $n_0$, the pitch D, the ridge slab width d, and the x-offset $\beta$) corresponding to expected ranges of profile shapes are also determined (1815). The intra-layer dependent portions of the rigorous coupled-wave calculation (i.e., the wave-vector matrices [A], eigenvector matrices [W], root-eigenvalue matrices [Q], and compound matrices [V]) are then pre-computed (1820) by the CPU 1515 for the determined ranges and samplings of the intra-layer parameters and incident-radiation parameters, and cached (1825) in the cache memory 1520. Ranges and samplings of aggregate-layer parameters (i.e., base width b, top width w, height h, and base-top offset c) corresponding to expected ranges of profile shapes are also determined (1827). Then, using the pre-computed and cached intra-layer portions of the rigorous coupled-wave calculation, aggregate-layer transfer matrices [$\Gamma_{li \to lj}$] corresponding to the determined range and sampling of aggregate-layer parameters are calculated (1828) by the CPU 1515 and cached (1829) in the cache memory 1520. Diffraction spectra are then calculated (1830) for combinations of aggregate-layer trapezoids 1030 to produce a sub-library of spectra. Each combination of aggregate-layer trapezoids 1030 is indexed (1835) in the cache memory 1520 with its associated spectrum to provide a library of profile-spectrum pairs. Diffraction signals are acquired (1805) by an optical setup, using either a reflectometry or an ellipsometry configuration, as depicted in FIGS. 1 and 2. The diffraction signal may be acquired prior to, during, or subsequent to the generation (1810), (1820), (1825), (1827), (1828), (1829), (1830) and (1835) of the profile-spectra library. Finally, a measured diffraction spectrum obtained from a physical profile is compared (1840) to the spectra in the library in order to select the spectrum in the library that best matches the measured diffraction spectrum. The combination of aggregate-layer trapezoids 1030 corresponding to the best-matched calculated spectrum is the estimate of the physical profile. The matching algorithms that can be used for this purpose range from simple least-squares approach (linear regression) to a neural network approach that compares features of the measured signal with the spectra from the library using a non-linear, principal-component regression scheme. Explanations of such methods may be found in numerous text books on the topic, such as Chapter 14 of "Mathematical Statistics and Data Analysis" by John Rice, Duxbury Press and Chapter 4 of "Neural Networks for Pattern Recognition" by Christopher Bishop, Oxford University Press.

It should be understood that the present invention is also applicable to off-axis or conical incident radiation 910 (i.e., the case where $\phi \neq 0$ and the plane of incidence 912 is not aligned with the direction of periodicity, $\hat{x}$, of the grating). The above exposition is straightforwardly adapted to the off-axis case since, as can be seen in "Rigorous Coupled-Wave Analysis of Planar-Grating Diffraction," M. G. Moharam and T. K. Gaylord, *J. Opt. Soc. Am.*, vol. 71, 811–818, July 1981, the differential equations for the electromagnetic fields in each layer have homogeneous solutions with coefficients and factors that are only dependent on intra-layer parameters and incident-radiation parameters. As with the case of on-axis incidence, aggregate-layer calculations are pre-calculated and cached. In computing the diffracted reflectivity from a periodic grating, cached aggregate-layer transfer matrices [$\Gamma_{li \to lj}$] corresponding to aggregate-layer trapezoids of the profile are retrieved for use in constructing a system matrix equation in a manner analogous to that described above.

Although the use of rigorous coupled-wave method of calculating the diffraction of radiation has been described, any method of diffraction calculation where the system equation involves the multiplication of a series of matrices, where each of these matrices is dependent on local parameters (such as intra-layer parameters) and/or global parameters (such as incident-radiation parameters) can be used. For example, the diffraction calculation may be an approximate method, and/or an integral formulations, or any other formulations, such as those mentioned in standard texts such as *Solid State Physics*, N. W. Ashcroft and N. D. Mermin, Saunders College, Philadelphia, 1976, pages 133–134, or *Optical Properties of Thin Solid Films*, O. S. Heavens, Dover Publications, Inc., New York, 1991, or *Ellipsometry and Polarized Light*, R. M. A. Azzam and N. M. Bashara, North-Holland Personal Library, Amsterdam, 1987. Furthermore, the present invention may be applied to diffraction calculations based on decompositions or analyses other than Fourier analysis, such as a decomposition into Bessel functions, Legendre polynomials, wavelets, etc.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. Many other variations are also to be considered within the scope of the present invention.

For instance: aggregate-layer transfer matrices may be generated and cached without caching of intra-layer calculations; the calculation of the present specification is applicable to circumstances involving conductive materials; once the aggregate-layer transfer matrices are calculated and cached, intermediate results (such as the permittivity, inverse permittivity, permittivity harmonics, inverse-permittivity harmonics, permittivity harmonics matrix, the inverse-permittivity harmonics matrix, the wave-vector matrix, eigenvalues of the wave-vector matrix, and/or eigenvalues of the wave-vector matrix) need not be stored; the compound matrix [V], which is equal to the product of the eigenvector matrix and the root-eigenvalue matrix, may be calculated when it is needed, rather than cached; the eigenvectors and eigenvalues of the matrix [A] may be calculated using another technique; a range of an incident-radiation parameter, intra-layer parameter and/or aggregate-layer parameter may consist of only a single value; the array of regularly-spaced incident-radiation parameter values, intra-layer parameter values and/or aggregate-layer parameter values for which the matrices, eigenvalues and eigenvectors are cached may be replaced with an array of irregularly-spaced incident-radiation parameter values, intra-layer parameter values and/or aggregate-layer parameter values, or a random selection of incident-radiation parameter values, intra-layer parameter values and/or aggregate-layer parameter values; the system equation may be solved for the diffracted reflectivity and/or the diffracted transmittance using any of a variety of matrix solution techniques; the "ridges" and "troughs" of the periodic grating may be ill-defined; the method of the present invention may be applied to gratings having two-dimensional periodicity; the method of the present invention may be applied to any polarization which is a superposition of TE and TM polarizations; the ridged structure of the periodic grating may be mounted on one or more layers of films deposited on the substrate; the method of the present invention may be used for diffractive analysis of lithographic masks or reticules; the method of the present invention may be applied to sound incident on a periodic grating; the method of the present invention may be applied to medical imaging techniques using incident sound or electromagnetic waves; the method of the present invention may be applied to assist in real-time tracking of fabrication processes; the gratings may be made by ruling, blazing or etching; the grating may be periodic on a curved surface, such as a spherical surface or a cylindrical surface, in which case expansions other than Fourier expansions would be used; the method of the present invention may be utilized in the field of optical analog computing, volume holographic gratings, holographic neural networks, holographic data storage, holographic lithography, Zernike's phase contrast method of observation of phase changes, the Schlieren method of observation of phase changes, the central dark-background method of observation, spatial light modulators, acousto-optic cells, etc. In summary, it is intended that the scope of the present invention be defined by the claims appended hereto and their equivalents.

We claim:

1. A method of generating a library of simulated-diffraction signals and hypothetical profiles of a periodic grating, said method comprising:
   generating diffraction calculations for a plurality of blocks of hypothetical layers,
      wherein each block of hypothetical layers includes two or more hypothetical layers, and
      wherein each hypothetical layer characterizes a layer within a hypothetical profile;
   storing the diffraction calculations generated for the blocks of hypothetical layers;
   generating a plurality of hypothetical profiles of the periodic grating;
   generating simulated-diffraction signals of each hypothetical profile based on the stored diffraction calculations for the blocks of hypothetical layers; and
   storing the plurality of hypothetical profiles and the simulated-diffraction signal for each hypothetical profile.

2. The method of claim 1, wherein generating diffraction calculations comprises:
   generating diffraction calculations for each hypothetical layer within each block of hypothetical layers; and
   aggregating the diffraction calculations of the hypothetical layers within each block of hypothetical layers to generate the diffraction calculation for the block of hypothetical layers.

3. The method of claim 1, wherein the blocks of hypothetical layers have trapezoidal shapes.

4. The method of claim 1, wherein the hypothetical layers have rectangular shapes.

5. The method of claim 1, wherein storing the diffraction calculations comprises:
   storing the diffraction calculations within a cache.

6. The method of claim 5, wherein the cache resides in a computer memory.

7. The method of claim 1, wherein generating a plurality of hypothetical profiles comprises:
   characterizing a hypothetical profile for the periodic grating with a set of parameters; and
   varying the set of parameters to generate the plurality of hypothetical profiles.

8. The method of claim 1, wherein generating simulated-diffraction signals comprises:
   for each hypothetical profile,
      selecting at least one block of hypothetical layers that characterizes the hypothetical profile;
      retrieving the diffraction calculation associated with the selected block of hypothetical layers; and
      applying boundary conditions to generate a simulated-diffraction signal for the hypothetical profile.

9. The method of claim 8, wherein selecting at least one block of hypothetical layers comprises:
   applying an error minimization algorithm to select one or more blocks of hypothetical layers to characterize the hypothetical profile.

10. The method of claim 8, wherein selecting at least one block of hypothetical layers comprises:

selecting a first block of hypothetical layers that characterizes a first layer of the hypothetical profile; and selecting at least a second block of hypothetical layers that characterizes at least a second layer of the hypothetical profile.

11. The method of claim 10, wherein the first layer and at least the second layer of the hypothetical profile are formed from the same material.

12. The method of claim 10, wherein the first layer of the hypothetical profile is formed from a first material and the second layer of the hypothetical profile is formed from a second material.

13. The method of claim 1, wherein storing the plurality of hypothetical profiles comprises:

pairing each hypothetical profile with the simulated-diffraction signal generated for that hypothetical profile, and storing the hypothetical profile and simulated-diffraction signal pair.

14. The method of claim 1, wherein the simulated-diffraction signals includes magnitude measurements.

15. The method of claim 14, wherein the simulated-diffraction signals includes phase measurements.

16. A method of generating a library of simulated-diffraction signals and hypothetical profiles of a periodic grating, said method comprising:

generating diffraction calculations for a plurality of blocks of hypothetical layers,
wherein each block of hypothetical layers includes two or more hypothetical layers;

storing the diffraction calculations generated for the blocks of hypothetical layers; and generating simulated-diffraction signals for a plurality of hypothetical profiles of the periodic grating, wherein for each hypothetical profile:
at least one block of hypothetical layers is selected that characterizes the hypothetical profile,
the diffraction calculation associated with the selected block of hypothetical layers is retrieved,
a simulated-diffraction signal for the hypothetical profile is generated based on the retrieved diffraction calculation, and
the hypothetical profile and the generated simulated-diffraction signal are stored.

17. The method of claim 16, wherein selecting at least one block of hypothetical layers comprises:

selecting a first block of hypothetical layers for a first hypothetical profile; and selecting at least a second block of hypothetical layers for the first hypothetical profile.

18. The method of claim 17, wherein the diffraction calculation associated with the first and second blocks of hypothetical layers are retrieved, and further comprising:

aggregating the diffraction calculations of the first and second blocks of hypothetical layers; and applying boundary conditions to generate the simulated-diffraction signal for the first hypothetical profile.

19. The method of claim 16, wherein the hypothetical profile includes a first layer formed from a first material and a second layer formed from a second material, and wherein selecting at least one block of hypothetical layers comprises:

selecting a first block of hypothetical layers for the first material that characterizes the first layer of the hypothetical profile; and selecting a second block of hypothetical layers for the second material that characterizes the second layer of the hypothetical profile.

20. The method of claim 16, wherein generating diffraction calculations comprises:

generating diffraction calculations for each hypothetical layer within each block of hypothetical layers; and aggregating the diffraction calculations for the hypothetical layers within each block of hypothetical layers.

21. The method of claim 16, wherein the diffraction calculations are generated and stored before generating simulated-diffraction signals.

22. The method of claim 21, wherein the diffraction calculations are stored in a cache.

23. The method of claim 22, wherein the hypothetical profile and generated simulated-diffraction signal are stored in a computer-readable medium.

24. A method of generating a library of simulated-diffraction signals for a periodic grating, said method comprising:

generating diffraction calculations for a plurality of hypothetical layers;

forming a plurality of blocks of hypothetical layers,
wherein two or more hypothetical layers are grouped together to form each block of hypothetical layers, and
wherein for each block of hypothetical layers:
the diffraction calculations of the hypothetical layers within the block of hypothetical layers is aggregated to generate a diffraction calculation for the block of hypothetical layers;

storing the diffraction calculations generated for the blocks of hypothetical layers;

generating a plurality of hypothetical profiles of the periodic grating;

generating a simulated-diffraction signal for each hypothetical profile based on the stored diffraction calculations for the blocks of hypothetical layers; and storing the generated simulated-diffraction signal.

25. The method of claim 24, wherein the blocks of hypothetical layers have trapezoidal shapes of varying dimensions.

26. The method of claim 25, wherein the hypothetical layers have rectangular shapes.

27. The method of claim 24, wherein generating a plurality of hypothetical profiles comprises:

characterizing a hypothetical profile for the periodic grating with a set of parameters; and varying the set of parameters to generate hypothetical profiles of varying shapes and dimensions.

28. The method of claim 24, wherein generating simulated-diffraction signals comprises:

for each hypothetical profile,
selecting at least one block of hypothetical layers that characterizes the hypothetical profile;
retrieving the diffraction calculation associated with the selected block of hypothetical layers; and
generating the simulated-diffraction signals for the hypothetical profile based on the retrieved diffraction calculation.

29. The method of claim 28, wherein selecting at least one block of hypothetical layers comprises:

selecting a plurality of blocks of hypothetical layers that characterize multiple layers within a hypothetical profile,
wherein the hypothetical profile can be formed from a single material or formed from two or more materials.

30. A system for generating a library of simulated-diffraction signals for a periodic grating, said system comprising:

a processor configured to generate diffraction calculations for a plurality of blocks of hypothetical layers,
wherein each block of hypothetical layers includes two or more hypothetical layers;
a memory configured to store the diffraction calculations generated for the blocks of hypothetical layers; and
wherein the processor is further configured to:
generate simulated-diffraction signals for a set of hypothetical profiles of the periodic grating based on the diffraction calculations stored in the memory.

31. The system of claim 30, wherein the processor comprises a plurality of processors.

32. The system of claim 31, wherein the processor comprises:
a first processor configured to generate simulated-diffraction signals for a first wavelength; and
a second processor configured to generate simulated diffraction signals for a second wavelength.

33. The system of claim 30, wherein for each hypothetical profile the processor is further configured to:
select at least one block of hypothetical layers from the memory that characterizes the hypothetical profile;
retrieve the diffraction calculation from the memory that is associated with the selected block of hypothetical layers;
apply boundary conditions to the retrieved diffraction calculation to generate the simulated-diffraction signal for the hypothetical profile; and
store the simulated-diffraction signal and the hypothetical profile.

34. The system of claim 33, wherein the processor is further configured to:
apply an error minimization algorithm to select the block of hypothetical layers.

35. The system of claim 30, wherein the processor is further configured to:
generate diffraction calculations for each hypothetical layer within each block of hypothetical layers; and
aggregate the diffraction calculations of the hypothetical layers within each block of hypothetical layers to generate the diffraction calculation for the block of hypothetical layers.

36. The system of claim 30, wherein the processor is further configured to:
generate and store the diffraction calculations for the blocks of hypothetical layers before generating the simulated-diffraction signals.

37. The system of claim 30, wherein the memory comprises a plurality of memories.

38. The system of claim 30, wherein the diffraction calculations stored in the memory is indexed by the shape and size of the blocks of hypothetical layers.

39. The system of claim 38, wherein blocks of hypothetical layers are generated for different types of materials used in forming the periodic grating, and wherein the diffraction calculations stored in the memory is indexed by material type.

40. A computer-readable storage medium containing computer executable instructions for causing a computer to generate a library of simulated-diffraction signals to be used in obtaining profiles of a periodic grating, comprising instructions for:
generating diffraction calculations for a plurality of hypothetical layers;
forming a plurality of blocks of hypothetical layers,
wherein two or more hypothetical layers are grouped together to form each block of hypothetical layers, and
wherein the diffraction calculations of the two or more hypothetical layers are aggregated together to generate a diffraction calculation for each block of hypothetical layers;
storing the diffraction calculations generated for the blocks of hypothetical layers;
generating a plurality of hypothetical profiles of the periodic grating; and
generating simulated-diffraction signals for each of the hypothetical profiles, further comprising:
selecting at least one block of hypothetical layers that characterizes the hypothetical profile,
retrieving the diffraction calculation associated with the selected block of hypothetical layers,
generating a simulated-diffraction signal for the hypothetical profile utilizing the retrieved diffraction calculation, and
storing the hypothetical profile and the generated simulated-diffraction signal.

41. The computer readable medium of claim 40, wherein the diffraction calculations for the blocks of hypothetical layers are stored in a cache.

42. The computer readable medium of claim 40, wherein the diffraction calculations for the blocks of hypothetical layers are generated and stored before generating the simulated-diffraction signals for the hypothetical profiles.

* * * * *